(12) United States Patent
Dierks et al.

(10) Patent No.: US 8,507,471 B2
(45) Date of Patent: Aug. 13, 2013

(54) BIPHENYLCARBOXAMIDE DERIVATIVES AS HEDGEHOD PATHWAY MODULATORS

(75) Inventors: Christine Dierks, Freiburg (DE); Markus Warmuth, Natick, MA (US); Xu Wu, San Diego, CA (US)

(73) Assignee: IRM LLC, Hamilton (BM)

( * ) Notice: Subject to any disclaimer, the term of this patent is extended or adjusted under 35 U.S.C. 154(b) by 524 days.

(21) Appl. No.: 12/663,490

(22) PCT Filed: Jun. 4, 2008

(86) PCT No.: PCT/US2008/065816
§ 371 (c)(1),
(2), (4) Date: Apr. 5, 2010

(87) PCT Pub. No.: WO2008/154259
PCT Pub. Date: Dec. 18, 2008

(65) Prior Publication Data
US 2010/0197659 A1   Aug. 5, 2010

Related U.S. Application Data

(60) Provisional application No. 60/942,654, filed on Jun. 7, 2007.

(51) Int. Cl.
*A01N 43/00*   (2006.01)

(52) U.S. Cl.
USPC .............. 514/211.15; 514/217.04; 514/238.2; 435/375

(58) Field of Classification Search
USPC .............. 514/211.15, 217.04, 238.2; 435/375
See application file for complete search history.

(56) References Cited

U.S. PATENT DOCUMENTS

| | | | |
|---|---|---|---|
| 8,178,563 B2 * | 5/2012 | Gao et al. ....................... | 514/352 |
| 2007/0038171 A1 | 2/2007 | Mayer | |

FOREIGN PATENT DOCUMENTS

| WO | WO2005/030206 A1 | 4/2005 |
|---|---|---|
| WO | WO2005/033288 A3 | 4/2005 |
| WO | WO2006/028958 A3 | 3/2006 |
| WO | WO2006/078283 A3 | 7/2006 |
| WO | WO2007/131201 A3 | 11/2007 |
| WO | WO2008/014291 A2 | 1/2008 |

OTHER PUBLICATIONS

Vippagunata et al, (Adv Drug Deliver Rev, 2001, 48, 3-26).*
International Search Report for International Application No. PCT/US2008/065816 dated Oct. 9, 2008.
Thayer et al, "Hedgehog is an early and late mediator of pancreatic cancer tumorigenesis", Nature, 425(6960):851-6 Oct. 23,2003.
Berman et al, "Widespread requirement for Hedgehog ligand stimulation in growth of digestive tract tumours", Nature, 425(6960):846-51 Oct. 23,2003.
Nakashima et al, "Nuclear factor-kappa B contributes to hedgehog signaling pathway activation through sonic hedgehog induction in pancreatic cancer," Cancer Research; 66 (14):7041-9 Jul. 18, 2006.
Feldmann et al, "Blockade of hedgehog signaling inhibits pancreatic cancer invasion and metastases: A new paradigm for combination therapy in solid cancers," Cancer Research; 67 (5):2187-96 Mar. 1, 2007.
Ji et al, "Oncogenic Kras suppresses GUI degradation and activates Hedgehog signaling pathway in pancreatic cancer cells", J Biol Chem; 282 (19): 14048-55 May 11, 2007.

* cited by examiner

*Primary Examiner* — Jeffrey S. Lundgren
*Assistant Examiner* — Ibrahim D Bori
(74) *Attorney, Agent, or Firm* — Matthew Mulkeen

(57) ABSTRACT

The invention provides a method for modulating the activity of the hedgehog signaling pathway. In particular, the invention provides a method for inhibiting aberrant growth states resulting from phenotypes such as Ptc loss-of-function, hedgehog gain-of-function, smoothened gain-of-function or Gli gain-of-function, comprising contacting a cell with a sufficient amount of a compound of Formula I.

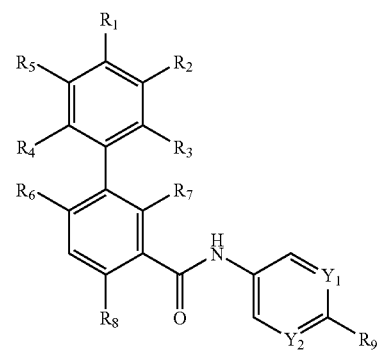

10 Claims, No Drawings

BIPHENYLCARBOXAMIDE DERIVATIVES AS HEDGEHOD PATHWAY MODULATORS

CROSS-REFERENCE TO RELATED APPLICATIONS

This application is a 371 U.S. national phase application of international application number PCT/US2008/065816 filed 4 Jun. 2008, which application claims priority to U.S. provisional patent application No. 60/942,654, filed 7 Jun. 2007. The full disclosure of these applications is incorporated herein by reference in its entirety and for all purposes.

BACKGROUND

1. Field of the Invention

The invention provides a method for modulating the activity of the hedgehog signaling pathway. In particular, the invention provides a method for inhibiting aberrant growth states resulting from phenotypes of Ptc loss-of-function, hedgehog gain-of-function, smoothened gain-of-function, Gli gain-of-function, or over expression of hedgehog ligands, comprising contacting a cell with a sufficient amount of a compound of Formula I.

2. Background of the Invention

During embryonic development, the hedgehog signaling pathway is essential for numerous processes such as the control of cell proliferation, differentiation and tissue patterning. The aberrant activity of the hedgehog signaling pathway, for example, as a result of enhanced activation, however may have pathological consequences. In this regard, activation of the hedgehog pathway in adult tissues can result in diseases such as psoriasis and specific types of cancer that include, but are not limited to, malignant lymphoma (LM), multiple myeloma (MM), cancers of the brain, muscle and skin, prostrate, medulloblastoma, pancreatic adenocarcinomas and small-cell lung carcinomas Enhanced activation of the hedgehog signaling pathway contributes to the pathology and/or symptomology of a number of diseases. Accordingly, molecules that modulate the activity of the hedgehog signaling pathway are useful as therapeutic agents in the treatment of such diseases.

SUMMARY OF THE INVENTION

In one aspect, the invention provides methods for inducing apoptosis of lymphoma or myeloma cells. These methods involve contacting the cells with an agent that inhibits hedgehog signaling pathway. Some of the methods are directed to inducing apoptosis of tumor cells that are present in a subject. Some of the methods are directed to inducing apoptosis of lymphoma or myeloma cells that do not express Gli3. Some of the methods employs a compound of Formula I to specifically inhibit the hedgehog signaling pathway:

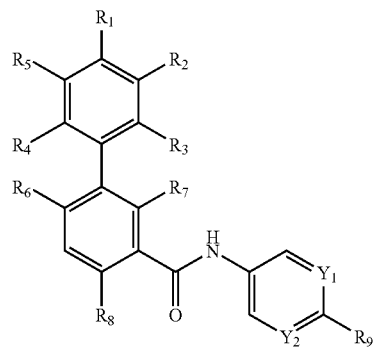

I in which $Y_1$ and $Y_2$ are independently selected from N and $CR_{10}$; wherein $R_{10}$ is selected from hydrogen, halo, $C_{1-6}$alkyl, halosubstituted-$C_{1-6}$alkyl, $C_{1-6}$alkoxy, halosubstituted-$C_{1-6}$alkoxy and —$OXNR_{10a}R_{10b}$; wherein $R_{10a}$ and $R_{10b}$ are independently selected from hydrogen and $C_{1-6}$alkyl;

$R_1$ is selected from cyano, halo, $C_{1-6}$alkyl, halosubstituted-$C_{1-6}$alkyl, $C_{1-6}$alkoxy, halosubstituted-$C_{1-6}$alkoxy, $C_{6-10}$aryl, dimethyl-amino, $C_{1-6}$alkyl-sulfanyl and $C_{3-8}$heterocycloalkyl optionally substituted with up to 2 $C_{1-6}$alkyl radicals;

$R_2$ and $R_5$ are independently selected from hydrogen, cyano, halo, $C_{1-6}$alkyl, halosubstituted-$C_{1-6}$alkyl, $C_{1-6}$alkoxy, halosubstituted-$C_{1-6}$alkoxy and dimethylamino;

$R_3$ and $R_4$ are independently selected from hydrogen, halo, cyano, $C_{1-6}$alkyl, halosubstituted-$C_{1-6}$alkyl, $C_{1-6}$alkoxy and halosubstituted-$C_{1-6}$alkoxy; or either $R_1$ and $R_2$ or $R_1$ and $R_5$ together with the phenyl to which they are both attached form $C_{5-10}$heteroaryl;

$R_6$ and $R_7$ are independently selected from hydrogen, $C_{1-6}$alkyl, halosubstituted-$C_{1-6}$alkyl, $C_{1-6}$alkoxy and halosubstituted-$C_{1-6}$alkoxy; with the proviso that $R_6$ and $R_7$ are not both hydrogen;

$R_8$ is selected from hydrogen, halo, $C_{1-6}$alkyl, halosubstituted-$C_{1-6}$alkyl, $C_{1-6}$alkoxy and halosubstituted-$C_{1-6}$alkoxy;

$R_9$ is selected from —$S(O)_2R_{11}$, —$C(O)R_{11}$, —$OR_{11}$, —$NR_{12a}R_{12b}$ and —$R_{11}$; wherein $R_{11}$ is selected from aryl, heteroaryl, cycloalkyl and heterocycloalkyl; $R_{12a}$ and $R_{12b}$ are independently selected from $C_{1-6}$alkyl and hydroxy-substituted-$C_{1-6}$alkyl;

wherein said aryl, heteroaryl, cycloalkyl and heterocycloalkyl of $R_9$ can be optionally substituted with 1 to 3 radicals independently selected from $C_{1-6}$alkyl, halosubstituted-$C_{1-6}$alkyl, $C_{1-6}$alkoxy, halosubstituted-$C_{1-6}$alkoxy, $C_{6-10}$aryl-$C_{0-4}$alkyl, $C_{5-10}$heteroaryl-$C_{0-4}$alkyl, $C_{3-12}$cycloalkyl and $C_{3-8}$heterocycloalkyl;

wherein said aryl-alkyl substituent of $R_9$ is optionally substituted with 1 to 3 radicals independently selected from halo, $C_{1-6}$alkyl, halosubstituted-$C_{1-6}$alkyl, $C_{1-6}$alkoxy, halosubstituted-$C_{1-6}$alkoxy and methyl-piperazinyl; and the N-oxide derivatives, prodrug derivatives, protected derivatives, individual isomers and mixture of isomers thereof; and the pharmaceutically acceptable salts and solvates (e.g. hydrates) of such compounds. Compounds of the invention also include all suitable isotopic variations of such compounds, and pharmaceutically acceptable salts, solvates, N-oxides, prodrugs and isomers thereof, and pharmaceutical compositions. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include but are not limited to isotopes of hydrogen, carbon, nitrogen and oxygen such as $^2H$, $^3H$, $^{11}C$, $^{13}C$, $^{14}C$, $^{15}N$, $^{17}O$, $^{18}O$, $^{35}S$, $^{18}F$, $^{36}Cl$ and $^{123}I$. Certain isotopic variations of the compounds of the invention and pharmaceutically acceptable salts thereof, for example, those in which a radioactive isotope such as $^3H$ or $^{14}C$ is incorporated, are useful in drug and/or substrate tissue distribution studies. In particular examples, $^3H$ and $^{14}C$ isotopes may be used for their ease of preparation and detectability. In other examples, substitution with isotopes such as may may afford certain therapeutic advantages resulting from greater metabolic stability, such as increased in vivo half-life or reduced dosage requirements. Isotopic variations of the compounds, and pharmaceutically acceptable salts, solvates, N-oxides, prodrugs and isomers thereof, and pharmaceutical compositions provided herein are prepared by conventional procedures using appropriate isotopic variations of suitable reagents.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating or ameliorating psoriasis, lymphoma or myeloma in a subject in which modulation of the hedgehog pathway activity, can prevent, inhibit or ameliorate the pathology and/or symptomology of psoriasis, lymphoma or myeloma, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating psoriasis, lymphoma or myeloma in an animal in which hedgehog pathway activity, contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DEFINITIONS

Unless defiled otherwise, all technical and scientific terms used herein have the same meaning as commonly understood by those of ordinary skill in the art to which this invention pertains. The following references provide one of skill with a general definition of many of the terms used in this invention: *Oxford Dictionary of Biochemistry and Molecular Biology*, Smith et al. (eds.), Oxford University Press (revised ed., 2000); *Dictionary of Microbiology and Molecular Biology*, Singleton et al. (Eds.), John Wiley & Sons ($3^{rd}$ ed., 2002); and *A Dictionary of Biology (Oxford Paperback Reference)*, Martin and Hine (Eds.), Oxford University Press ($4^{th}$ ed., 2000). In addition, the following definitions are provided to assist the reader in the practice of the invention.

The term "agent" or "test agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" can be used interchangeably.

"Alkyl" as a group and as a structural element of other groups, for example halo-substituted-alkyl and alkoxy, can be either straight-chained or branched. $C_{1-4}$-alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"Cancer", as used herein, includes solid mammalian tumors as well as hematological malignancies. "Solid mammalian tumors" include cancers of the head and neck, lung, mesothelioma, mediastinum, esophagus, stomach, pancreas, hepatobiliary system, small intestine, colon, colorectal, rectum, anus, kidney, urethra, bladder, prostate, urethra, penis, testis, gynecological organs, ovaries, breast, endocrine system, skin, central nervous system including brain; sarcomas of the soft tissue and bone; and melanoma of cutaneous and intraocular origin. "Hematological malignancies" includes childhood leukemia and lymphomas, Hodgkin's disease, lymphomas of lymphocytic and cutaneous origin, acute and chronic leukemia, plasma cell neoplasm and cancers associated with AIDS. In addition, a cancer at any stage of progression can be treated, such as primary, metastatic, and recurrent cancers. Information regarding numerous types of cancer can be found, e.g., from the American Cancer Society, or from, e.g., Wilson et al. (1991) Harrison's Principles of Internal Medicine, 12th Edition, McGraw-Hill, Inc. Both human and veterinary uses are contemplated. Cancers which are particularly amenable to treatment by the compounds and methods of the invention include but are not limited to gliomas, medulloblastomas, primitive neuroectodermal tumors (PNETS), basal cell carcinoma (BCC), small cell lung cancers, large cell lung cancers, tumors of the gastrointestinal tract, rhabdomyosarcomas, soft tissue sarcomas, pancreatic tumors, bladder tumors and prostate tumors. As used herein, the term "malignant hyperproliferative disorder(s)" includes but is not limited to cancers, neuronal proliferative disorders, bone marrow proliferative diseases and leukemias. As used herein, the term "non-malignant hyperproliferative disorder(s)" includes but is not limited to non-malignant and non-neoplastic proliferative disorders, such as smooth muscle hyperplasia in blood vessels, cutaneous scarring, and pulmonary fibrosis.

As used herein, "contacting" has its normal meaning and refers to combining two or more molecules (e.g., a small molecule organic compound and a polypeptide) or combining molecules and cells (e.g., a compound and a cell). Contacting can occur in vitro, e.g., combining two or more agents or combining a compound and a cell or a cell lysate in a test tube or other container. Contacting can also occur in a cell or in situ, e.g., contacting two polypeptides in a cell by coexpression in the cell of recombinant polynucleotides encoding the two polypeptides, or in a cell lysate.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc.

"Hedgehog-related disorder(s)" as used herein includes disorders associated with disruption or aberrance of the Hedgehog pathway, as well as disorders associated with normal but undesired growth states relating to activation of the Hedgehog pathway. "Hedgehog-related disorder(s)" include but are not limited to tumor formation, cancer, neoplasia, malignant hyperproliferative disorders, and non-malignant hyperproliferative disorders. "Hedgehog-related disorder(s)" also include benign prostate hyperplasia, psoriasis, wet macular degeneration, osteopetrosis and unwanted hair growth.

"Heteroaryl" is as defined for aryl above where one or more of the ring members is a heteroatom. For example $C_{5-10}$heteroaryl is a minimum of 5 members as indicated by the carbon atoms but that these carbon atoms can be replaced by a heteroatom. Consequently, $C_{5-10}$heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, pyrrolidinyl-2-one, piperazinyl, piperidinyl, piperidinylone, 1,4-dioxa-8-aza-spiro[4.5]dec-8-yl, thiomorpholino, sulfanomorpholino, sulfonomorpholino, etc.

"Halogen" (or halo) preferably represents chloro or fluoro, but may also be bromo or iodo.

The term "hedgehog" is used to refer generically to any member of the hedgehog family, including sonic, indian, desert and tiggy winkle. The term may be used to indicate protein or gene. The term is also used to describe homolog/ortholog sequences in different animal species.

The terms "hedgehog (Hh) signaling pathway" and "hedgehog (Hh) signaling" are used interchangeably and refer to the chain of events normally mediated by various members of the signaling cascade such as hedgehog, patched (Ptch), smoothened (Smo), and Gli. The hedgehog pathway can be activated even in the absence of a hedgehog protein by activating a downstream component. For example, overexpression of Smo will activate the pathway in the absence of hedgehog.

Hh signaling components or members of Hh signaling pathway refer to gene products that participate in the Hh signaling pathway. An Hh signaling component frequently materially or substantially affects the transmission of the Hh signal in cells/tissues, typically resulting in changes in degree of downstream gene expression level and/or phenotypic changes. Hh signaling components, depending on their biological function and effects on the final outcome of the downstream gene activation/expression, may be divided into positive and negative regulators. A positive regulator is an Hh signaling component that positively affects the transmission of the Hh signal, i.e., stimulates downstream biological events when Hh is present. Examples include hedgehog, Smo, and Gli. A negative regulator is an Hh signaling component that negatively affects the transmission of the Hh signal, i.e., inhibits downstream biological events when Hh is present. Examples include (but are not limited to) Ptch and SuFu.

Hedgehog signaling antagonists, antagonists of Hh signaling or inhibitors of Hh signaling pathway refer to agents that inhibit the bioactivity of a positive Hh signaling component (such as hedgehog, Ptch, or Gli) or down-regulate the expression of the Hh signaling component. They also include agents which up-regulate a negative regulator of Hh signaling component. A hedgehog signaling antagonists may be directed to a protein encoded by any of the genes in the hedgehog pathway, including (but not limited to) sonic, indian or desert hedgehog, smoothened, ptch-1, ptch-2, gli-1, gli-2, gli-3, etc.

"Hedgehog gain-of-function" refers to an aberrant modification or mutation of a Ptc gene, hedgehog gene, or smoothened gene, or a decrease (or loss) in the level of expression of such a gene, which results in a phenotype which resembles contacting a cell with a hedgehog protein, e.g., aberrant activation of a hedgehog pathway. The gain-of-function may include a loss of the ability of the Ptc gene product to regulate the level of expression of Gli genes, e.g., Gli1, Gli2, and Gli3. The term 'hedgehog gain-of-function' is also used herein to refer to any similar cellular phenotype (e.g., exhibiting excess proliferation) which occurs due to an alteration anywhere in the hedgehog signal transduction pathway, including, but not limited to, a modification or mutation of hedgehog itself. For example, a tumor cell with an abnormally high proliferation rate due to activation of the hedgehog signaling pathway would have a 'hedgehog gain-of-function' phenotype, even if hedgehog is not mutated in that cell.

"Patched loss-of-function" refers to an aberrant modification or mutation of a Ptc gene, or a decreased level of expression of the gene, which results in a phenotype which resembles contacting a cell with a hedgehog protein, e.g., aberrant activation of a hedgehog pathway. The loss-of-function may include a loss of the ability of the Ptc gene product to regulate the level of expression of Gli genes, e.g., Gli1, Gli2 and Gli3.

"Gli gain-of-function" refers to an aberrant modification or mutation of a Gli gene, or an increased level of expression of the gene, which results in a phenotype which resembles contacting a cell with a hedgehog protein, e.g., aberrant activation of a hedgehog pathway.

The term "inhibiting" or "inhibition," in the context of tumor growth or tumor cell growth, refers to delayed appearance of primary or secondary tumors, slowed development of primary or secondary tumors, decreased occurrence of primary or secondary tumors, slowed or decreased severity of secondary effects of disease, or arrested tumor growth and regression of tumors. The term "prevent" or "prevention" refers to a complete inhibition of development of primary or secondary tumors or any secondary effects of disease. In the context of modulation of enzymatic activities, inhibition relates to reversible suppression or reduction of an enzymatic activity including competitive, uncompetitive, and noncompetitive inhibition. This can be experimentally distinguished by the effects of the inhibitor on the reaction kinetics of the enzyme, which may be analyzed in terms of the basic Michaelis-Menten rate equation. Competitive inhibition occurs when the inhibitor can combine with the free enzyme in such a way that it competes with the normal substrate for binding at the active site. A competitive inhibitor reacts reversibly with the enzyme to form an enzyme-inhibitor complex [EI], analogous to the enzyme-substrate complex.

"Smoothened gain-of-function" refers to an aberrant modification or mutation of a Smo gene, or an increased level of expression of the gene, which results in a phenotype which resembles contacting a cell with a hedgehog protein, e.g., aberrant activation of a hedgehog pathway.

The term "subject" includes mammals, especially humans. It also encompasses other non-human animals such as cows, horses, sheep, pigs, cats, dogs, mice, rats, rabbits, guinea pigs, monkeys.

The term "treat" or "treatment" refers to arrested tumor growth, and to partial or complete regression of tumors. The term "treating" includes the administration of compounds or agents to prevent or delay the onset of the symptoms, complications, or biochemical indicia of a disease (e.g., lymphoma and myeloma), alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

The present invention relates to the discovery that signal transduction pathways regulated by hedgehog, patched (Ptc), gli and/or smoothened can be modulated by compounds of Formula I.

DESCRIPTION OF PREFERRED EMBODIMENTS

The therapeutic methods of the invention employ an antagonist of the hedgehog signaling pathway to inhibit growth and proliferation of psoriasis, lymphoma cells, leukemia cells, or myeloma cells. These methods involve contacting such a tumor cell (in vitro or in vivo) with an inhibitor of the Hh signaling pathway, a compound of Formula I. In one embodiment, with respect to compounds of Formula I, $Y_1$ and $Y_2$ are selected from N and $CR_{10}$; wherein $R_{10}$ is selected from hydrogen, methyl, fluoro, chloro, bromo, dimethylamino-ethoxy and trifluoromethyl; $R_6$ and $R_7$ are independently selected from hydrogen methyl, chloro, fluoro, bromo, trifluoromethyl and methoxy; with the proviso that $R_6$ and $R_7$ are not both hydrogen; and $R_8$ is selected from hydrogen, fluoro, chloro, methyl and trifluoromethyl.

In another embodiment, $R_1$ is selected from cyano, chloro, fluoro, methyl, ethyl, t-butyl, propyl, isobutyl, isopropyl, isopropyloxy, butoxy, methoxy, dimethyl-amino, ethoxy, methyl-sulfanyl, phenyl, trifluoromethyl, trifluoromethoxy and piperazinyl optionally substituted with up to 2 methyl radicals; $R_2$ and $R_5$ are independently selected from hydrogen, chloro, fluoro, cyano, methyl, trifluoromethyl, isopropyloxy, methoxy, ethoxy, trifluoromethoxy and dimethylamino; and $R_3$ and $R_4$ are independently selected from hydrogen, chloro, methyl, methoxy and cyano; or either $R_1$ and $R_2$ or $R_1$ and $R_5$ together with the phenyl to which they are both attached form quinoxalinyl.

In another embodiment, $R_9$ is selected from $—S(O)_2R_{11}$, $—OR_{11}$, $—C(O)R_{11}$, $—NR_{12a}R_{12b}$ and $—R_{11}$; wherein $R_{11}$ is selected from thiomorpholino, sulfonomorpholino, sulfanomorpholino, morpholino, cyclohexyl, phenyl, azepan-1-yl, 2-oxopiperazin-1-yl, 1,4-oxazepan-4-yl, piperidin-1-yl, tetrahydro-2H-pyran-4-yl, piperidin-3-yl, piperazinyl, pyrrolidinyl and 1,4-diazepan-1-yl; $R_{12a}$ and $R_{12b}$ are independently selected from isobutyl and hydroxy-ethyl; wherein said thiomorpholino, sulfonomorpholino, sulfanomorpholino, morpholino, cyclohexyl, phenyl, azepan-1-yl, 2-oxopiperazin-1-yl, 1,4-oxazepan-4-yl, piperidin-1-yl, tetrahydro-2H-pyran-4-yl, piperidin-3-yl, piperazinyl, pyrrolidinyl or 1,4-diazepan-1-yl of $R_9$ can be optionally substituted with 1 to 3 radicals independently selected from methyl, ethyl, methoxy, benzyl, thienyl-methyl, pyridinyl-methyl, benzo[d][1,3]dioxol-6-yl and 2,3-dihydrobenzo[b][1,4]dioxin-7-yl; wherein said phenyl or benzyl substituent of $R_9$ is optionally substituted with 1 to 3 radicals independently selected from methoxy, ethoxy, methyl-piperazinyl, methyl, trifluoromethoxy, chloro, fluoro and trifluoromethyl.

Preferred compounds of Formula I are selected from 4'-cyano-6-methyl-biphenyl-3-carboxylic acid [4-(morpholine-4-sulfonyl)-phenyl]-amide, 4'-cyano-6-methyl-biphenyl-3-carboxylic acid [6-(2,6-dimethyl-morpholin-4-yl)-pyridin-3-yl]-amide, 4'-Cyano-2-methyl-biphenyl-3-carboxylic acid (6-azepan-1-yl-pyridin-3-yl)-amide, 4'-Methoxy-2-methyl-biphenyl-3-carboxylic acid (6-azepan-1-yl-pyridin-3-yl)-amide, 4'-Methoxy-2-methyl-biphenyl-3-carboxylic acid (4-cyclohexyl-phenyl)-amide, 4'-Methoxy-2-methyl-biphenyl-3-carboxylic acid [6-(2-methyl-morpholin-4-yl)-pyridin-3-yl]-amide, 4'-Dimethylamino-2-methyl-biphenyl-3-carboxylic acid (4-cyclohexyl-phenyl)-amide, 4'-Dimethylamino-2-methyl-biphenyl-3-carboxylic acid (4-morpholin-4-yl-phenyl)-amide, 6-Chloro-4'-dimethylamino-biphenyl-3-carboxylic acid (6-[1,4]oxazepan-4-yl-pyridin-3-yl)-amide, 6-Chloro-4'-dimethylamino-biphenyl-3-carboxylic acid (6-morpholin-4-yl-pyridin-3-yl)-amide, 6-Chloro-4'-dimethylamino-biphenyl-3-carboxylic acid (6-azepan-1-yl-pyridin-3-yl)-amide, 6-Chloro-4'-methoxy-biphenyl-3-carboxylic acid [6-(2-methyl-morpholin-4-yl)-pyridin-3-yl]-amide, 6-Chloro-4'-methoxy-biphenyl-3-carboxylic acid (6-[1,4]oxazepan-4-yl-pyridin-3-yl)-amide, 6-Chloro-4'-methoxy-biphenyl-3-carboxylic acid (6-azepan-1-yl-pyridin-3-yl)-amide, 6-Chloro-4'-methoxy-biphenyl-3-carboxylic acid (6-morpholin-4-yl-pyridin-3-yl)-amide, 4'-Methoxy-6-methyl-biphenyl-3-carboxylic acid (6-morpholin-4-yl-pyridin-3-yl)-amide, 4'-Methoxy-6-methyl-biphenyl-3-carboxylic acid (6-[1,4]oxazepan-4-yl-pyridin-3-yl)-amide, 4'-Methoxy-6-methyl-biphenyl-3-carboxylic acid [6-(2-methyl-morpholin-4-yl)-pyridin-3-yl]-amide, 4'-Dimethylamino-6-methyl-biphenyl-3-carboxylic acid [6-(2-methyl-morpholin-4-yl)-pyridin-3-yl]-amide, 4'-Dimethylamino-6-methyl-biphenyl-3-carboxylic acid (6-[1,4]oxazepan-4-yl-pyridin-3-yl)-amide, 4'-Dimethylamino-6-methyl-biphenyl-3-carboxylic acid (6-morpholin-4-yl-pyridin-3-yl)-amide, 4'-Methoxy-6-methyl-biphenyl-3-carboxylic acid (6-azepan-1-yl-pyridin-3-yl)-amide, 4'-Ethoxy-6-methyl-biphenyl-3-carboxylic acid (6-azepan-1-yl-pyridin-3-yl)-amide, 6-Methyl-4'-methylsulfanyl-biphenyl-3-carboxylic acid (6-azepan-1-yl-pyridin-3-yl)-amide, 4'-Dimethylamino-6-methyl-biphenyl-3-carboxylic acid (6-azepan-1-yl-pyridin-3-yl)-amide, 6-Methyl-[1,1';4',1'']terphenyl-3-carboxylic acid (6-azepan-1-yl-pyridin-3-yl)-amide, 3'-Chloro-6-methyl-biphenyl-3-carboxylic acid (6-azepan-1-yl-pyridin-3-yl)-amide, 2',4'-Dichloro-6-methyl-biphenyl-3-carboxylic acid (6-azepan-1-yl-pyridin-3-yl)-amide, 2'-Chloro-6-methyl-biphenyl-3-carboxylic acid (6-azepan-1-yl-pyridin-3-yl)-amide, 3'-Chloro-6-methyl-biphenyl-3-carboxylic acid (6-azepan-1-yl-pyridin-3-yl)-amide, 3',4'-Dichloro-6-methyl-biphenyl-3-carboxylic acid (6-azepan-1-yl-pyridin-3-yl)-amide, 3'-Chloro-6-methyl-4'-trifluoromethyl-biphenyl-3-carboxylic acid (6-azepan-1-yl-pyridin-3-yl)-amide, 6,4'-Dimethyl-biphenyl-3-carboxylic acid (6-azepan-1-yl-pyridin-3-yl)-amide, 4'-Ethyl-6-methyl-biphenyl-3-carboxylic acid (6-azepan-1-yl-pyridin-3-yl)-amide, 4'-tert-Butyl-6-methyl-biphenyl-3-carboxylic acid (6-azepan-1-yl-pyridin-3-yl)-amide, 6-Methyl-4'-propyl-biphenyl-3-carboxylic acid (6-azepan-1-yl-pyridin-3-yl)-amide, 4'-Isobutyl-6-methyl-biphenyl-3-carboxylic acid (6-azepan-1-yl-pyridin-3-yl)-amide, 4'-Isopropyl-6-methyl-biphenyl-3-carboxylic acid (6-azepan-1-yl-pyridin-3-yl)-amide, 6,2',6'-Trimethyl-biphenyl-3-carboxylic acid (6-azepan-1-yl-pyridin-3-yl)-amide, 6,2',3'-Trimethyl-biphenyl-3-carboxylic acid (6-azepan-1-yl-pyridin-3-yl)-amide, 6-Methyl-4'-trifluoromethyl-biphenyl-3-carboxylic acid (6-azepan-1-yl-pyridin-3-yl)-amide, 6-Methyl-3'-trifluoromethyl-biphenyl-3-carboxylic acid (6-azepan-1-yl-pyridin-3-yl)-amide, 6-Methyl-3',5'-bistrifluoromethyl-biphenyl-3-carboxylic acid (6-azepan-1-yl-pyridin-3-yl)-amide, 3'-Isopropoxy-6-methyl-biphenyl-3-carboxylic acid (6-azepan-1-yl-pyridin-3-yl)-amide, 3'-Ethoxy-6-methyl-biphenyl-3-carboxylic acid (6-azepan-1-yl-pyridin-3-yl)-amide, 2',6'-Dimethoxy-6-methyl-biphenyl-3-carboxylic acid (6-azepan-1-yl-pyridin-3-yl)-amide, 6-Methyl-4'-trifluoromethoxy-biphenyl-3-carboxylic acid (6-azepan-1-yl-pyridin-3-yl)-amide, 6-Methyl-3'-trifluoromethoxy-biphenyl-3-carboxylic acid (6-azepan-1-yl-pyridin-3-yl)-amide, 6-Methyl-biphenyl-3-carboxylic acid (4-morpholin-4-yl-phenyl)-amide, 4'-Methoxy-6-methyl-biphenyl-3-carboxylic acid (4-morpholin-4-yl-phenyl)-amide, 3'-Methoxy-6-methyl-biphenyl-3-carboxylic acid (4-morpholin-4-yl-phenyl)-amide, 4'-(2-Dimethylamino-ethoxy)-6-methyl-biphenyl-3-carboxylic acid (4-morpholin-4-yl-phenyl)-amide, 3'-Dimethylamino-6-methyl-biphenyl-3-carboxylic acid (4-morpholin-4-yl-phenyl)-amide, 4'-Fluoro-6-methyl-biphenyl-3-carboxylic acid (4-morpholin-4-yl-phenyl)-amide, 3'-Fluoro-6-methyl-biphenyl-3-carboxylic acid (4-morpholin-4-yl-phenyl)-amide, 2'-Fluoro-6-methyl-biphenyl-3-carboxylic acid (4-morpholin-4-yl-phenyl)-amide, 4-Methyl-N-(4-morpholin-4-yl-phenyl)-3-quinoxalin-6-yl-benzamide, 6-Methyl-4'-(4-methyl-piperazin-1-yl)-biphenyl-3-carboxylic acid (4-morpholin-4-yl-phenyl)-amide, 2'-Cyano-6-methyl-biphenyl-3-carboxylic acid (4-morpholin-4-yl-phenyl)-amide, 3'-Cyano-6-methyl-biphenyl-3-carboxylic acid (4-morpholin-4-yl-phenyl)-amide, 4'-Cyano-6-methyl-biphenyl-3-carboxylic acid (6-[1,4]oxazepan-4-yl-pyridin-3-yl)-amide, 4'-Cyano-6-methyl-biphenyl-3-carboxylic acid (6-azepan-1-yl-pyridin-3-yl)-amide, 4'-Cyano-6-methyl-biphenyl-3-carboxylic acid [6-(2-methyl-morpholin-4-yl)-pyridin-3-yl]-amide, 4'-Cyano-6-methyl-biphenyl-3-carboxylic acid (3,4,5,6-tetrahydro-2H-[1,2]bipyridinyl-5'-yl)-amide, 4'-Cyano-6-methyl-biphenyl-3-carboxylic acid (6-morpholin-4-yl-pyridin-3-yl)-amide, 4'-Cyano-6-methyl-biphenyl-3-carboxylic acid [6-(4-methyl-piperazin-1-yl)-pyridin-3-yl]-amide, 4'-Cyano-6-methyl-biphenyl-3-carboxylic acid (4-morpholin-4-yl-phenyl)-amide, 4'-Cyano-6-methyl-biphenyl-3-carboxylic acid (3-fluoro-4-morpholin-4-yl-phenyl)-amide, 4'-Cyano-6-methyl-biphenyl-3-carboxylic acid (3-chloro-4-morpholin-4-yl-phenyl)-amide, 4'-Cyano-6-methyl-biphenyl-3-carboxylic acid (3-bromo-4-morpholin-4-yl-phenyl)-amide, 4'-Cyano-6-methyl-biphenyl-3-carboxylic acid (3-methyl-4-morpholin-4-yl-phenyl)-amide, 4'-Cyano-6-methyl-biphenyl-3-carboxylic acid (4-morpholin-4-yl-3-trifluoromethyl-phenyl)-amide, 4'-Cyano-6-methyl-biphenyl-3-carboxylic acid (4-cyclohexyl-phenyl)-amide, 4'-Cyano-6-methyl-biphenyl-3-carboxylic acid biphenyl-4-ylamide, 4'-Cyano-6-methyl-biphenyl-3-carboxylic acid (4'-methoxy-biphenyl-4-yl)-amide, 4'-Cyano-6-methyl-biphenyl-3-carboxylic acid [4-(4-benzyl-piperazin-1-yl)-phenyl]-amide, 4'-Cyano-6-methyl-biphenyl-3-carboxylic acid [4-(piperidine-1-sulfonyl)-phenyl]-amide, 4'-Cyano-6-methyl-biphenyl-3-carboxylic acid [4-(pyrrolidine-1-sulfonyl)-phenyl]-amide, 4'-Cyano-6-methoxy-biphenyl-3-carboxylic acid (6-azepan-1-yl-pyridin-3-yl)-amide, 4'-Cyano-2-methoxy-biphenyl-3-carboxylic acid (6-azepan-1-yl-pyridin-3-yl)-amide, 4'-Cyano-2-methyl-biphenyl-3-carboxylic acid (6-azepan-1-yl-pyridin-3-yl)-amide, 3'-Fluoro-4'-methoxy-6-methyl-biphenyl-3-carboxylic acid (6-azepan-1-yl-pyridin-3-yl)-amide, 4'-Isopropoxy-6-methyl-biphenyl-3-carboxylic acid (6-azepan-1-yl-pyridin-3-yl)-amide, 4'-Butoxy-6-methyl-biphenyl-3-carboxylic acid (6-azepan-1-yl-pyridin-3-yl)-amide, 3'-Chloro-4'-methoxy-6-methyl-biphenyl-3-carboxylic acid (6-azepan-1-yl-pyridin-3-yl)-amide, 4'-Methoxy-6,3'-dimethyl-biphenyl-3-carboxylic acid (6-azepan-1-yl-pyridin-3-yl)-amide, 4'-Cyano-2-methyl-biphenyl-3-carboxylic acid [4-(piperidine-1-sulfonyl)-phenyl]-amide, 4'-Cyano-6-fluoro-biphenyl-3-carboxylic acid [4-(piperidine-1-sulfonyl)-phenyl]-amide, 6-Bromo-4'-cyano-biphenyl-3-carboxylic acid [4-(piperidine-1-sulfonyl)-phenyl]-amide, 4'-Cyano-6-methyl-biphenyl-3-carboxylic acid [6-(4-benzyl-[1,4]diazepan-1-yl)-pyridin-3-yl]-amide, 4'-Cyano-6-methyl-biphenyl-3-carboxylic acid [6-(4-thiophen-3-ylmethyl-[1,4]diazepan-1-yl)-pyridin-3-yl]-amide, 4'-Cyano-2-methyl-biphenyl-3-carboxylic acid [6-(2,6-dimethyl-morpholin-4-yl)-pyridin-3-yl]-amide, 4'-Methoxy-2-methyl-biphenyl-3-carboxylic acid [6-(2,6-dimethyl-morpholin-4-yl)-pyridin-3-yl]-amide, 2-Methyl-4'-trifluoromethyl-biphenyl-3-carboxylic acid [6-(2,6-dimethyl-morpholin-4-yl)-pyridin-3-yl]-amide, 2-Methyl-4'-trifluoromethoxy-biphenyl-3-carboxylic acid [6-(2,6-dimethyl-morpholin-4-yl)-pyridin-3-yl]-amide, 4'-Cyano-2-methyl-biphenyl-3-carboxylic acid [6-(2-methyl-morpholin-4-yl)-pyridin-3-yl]-amide, 4'-Cyano-2-fluoro-biphenyl-3-carboxylic acid [4-(piperidine-1-sulfonyl)-phenyl]-amide, 4'-Cyano-6-trifluoromethyl-biphenyl-3-carboxylic acid [4-(piperidine-1-sulfonyl)-phenyl]-amide, 4'-Cyano-6-methyl-biphenyl-3-carboxylic acid {6-(4-pyridin-4-ylmethyl-[1,4]diazepan-1-yl)-pyridin-3-yl}-amide, 4'-Cyano-6-methyl-biphenyl-3-carboxylic acid {6-(4-pyridin-3-ylmethyl-[1,4]diazepan-1-yl)-pyridin-3-yl}-amide, 4'-Cyano-6-methyl-biphenyl-3-carboxylic acid {6-[4-(2,6-dimethoxy-benzyl)-[1,4]diazepan-1-yl]-pyridin-3-yl}-amide, 4'-Cyano-6-methyl-biphenyl-3-carboxylic acid {6-[4-(2-ethoxy-benzyl)-[1,4]diazepan-1-yl]-pyridin-3-yl}-amide, 4'-Cyano-6-methyl-biphenyl-3-carboxylic acid (6-{4-[2-(4-methyl-piperazin-1-yl)-benzyl]-[1,4]diazepan-1-yl}-pyridin-3-yl)-amide, 4'-Cyano-6-methyl-biphenyl-3-carboxylic acid {6-[4-(4-methoxy-2,3-dimethyl-benzyl)-[1,4]diazepan-1-yl]-pyridin-3-yl}-amide, 4'-Cyano-6-methyl-biphenyl-3-carboxylic acid {6-[4-(2,3-dihydro-benzo[1,4]dioxin-6-ylmethyl)-[1,4]diazepan-1-yl]-pyridin-3-yl}-amide, 4'-Cyano-6-methyl-biphenyl-3-carboxylic acid {6-(4-pyridin-2-ylmethyl-[1,4]diazepan-1-yl)-pyridin-3-yl}-amide, 4'-Cyano-6-methyl-biphenyl-3-carboxylic acid {6-(4-benzo[1,3]dioxol-4-ylmethyl-[1,4]diazepan-1-yl)-pyridin-3-yl}-amide, 4'-Cyano-6-methyl-biphenyl-3-carboxylic acid {6-[4-(2-trifluoromethoxy-benzyl)-[1,4]diazepan-1-yl]-pyridin-3-yl}-amide, 4'-Cyano-6-methyl-biphenyl-3-carboxylic acid {6-[4-(2-dimethylamino-benzyl)-[1,4]diazepan-1-yl]-pyridin-3-yl}-amide, 4'-Cyano-6-methyl-biphenyl-3-carboxylic acid {6-[4-(2-chloro-5-trifluoromethyl-benzyl)-[1,4]diazepan-1-yl]-pyridin-3-yl}-amide, 4'-Cyano-6-methyl-biphenyl-3-carboxylic acid {6-[4-(2,3-difluoro-benzyl)-[1,4]diazepan-1-yl]-pyridin-3-yl}-amide, 4'-Cyano-6-methyl-biphenyl-3-carboxylic acid {6-[4-(2-chloro-4-fluoro-benzyl)-[1,4]diazepan-1-yl]-pyridin-3-yl}-amide, 4'-Cyano-6-methyl-biphenyl-3-carboxylic acid {6-[4-(2,6-difluoro-benzyl)-[1,4]diazepan-1-yl]-pyridin-3-yl}-amide, 2-Chloro-4'-cyano-biphenyl-3-carboxylic acid [4-(piperidine-1-sulfonyl)-phenyl]-amide, 4'-Cyano-6-trifluoromethyl-biphenyl-3-carboxylic acid [6-(2,6-dimethyl-morpholin-4-yl)-pyridin-3-yl]-amide, 2-Chloro-4'-cyano-biphenyl-3-carboxylic acid [6-(2,6-dimethyl-morpholin-4-yl)-pyridin-3-yl]-amide, 4'-Cyano-6-ethyl-biphenyl-3-carboxylic acid [6-(2,6-dimethyl-morpholin-4-yl)-pyridin-3-yl]-amide, 4'-Cyano-6-methyl-biphenyl-3-carboxylic acid {6-[4-(3-fluoro-benzyl)-piperazin-1-yl]-pyridin-3-yl}-amide, 4'-Cyano-6-methyl-biphenyl-3-carboxylic acid {6-[4-(2-trifluoromethoxy-benzyl)-piperazin-1-yl]-pyridin-3-yl}-amide, 4'-Cyano-6-methyl-biphenyl-3-carboxylic acid {6-[4-(3-chloro-benzyl)-piperazin-1-yl]-pyridin-3-yl}-amide, 4'-Cyano-6-methyl-biphenyl-3-carboxylic acid {6-[4-(4-isobutyl-benzyl)-piperazin-1-yl]-pyridin-3-yl}-amide, 4'-Cyano-6-methyl-biphenyl-3-carboxylic acid {6-[4-(4-tert-butyl-benzyl)-piperazin-1-yl]-pyridin-3-yl}-amide, 4'-Cyano-6-methyl-biphenyl-3-carboxylic acid {6-[4-(7-methoxy-benzo[1,3]dioxol-5-ylmethyl)-piperazin-1-yl]-pyridin-3-yl}-amide, 4'-Cyano-6-methyl-biphenyl-3-carboxylic acid [6-(4-benzyl-piperazin-1-yl)-pyridin-3-yl]-amide, 4'-Cyano-6-methyl-biphenyl-3-carboxylic acid [6-(4-pyridin-3-ylmethyl-piperazin-1-yl)-pyridin-3-yl]-amide, 4'-Cyano-6-methyl-biphenyl-3-carboxylic acid {6-[4-(4-difluoromethoxy-benzyl)-piperazin-1-yl]-pyridin-3-yl}-amide, 4'-Cyano-6-methyl-biphenyl-3-carboxylic acid {6-[4-(4-cyano-benzyl)-piperazin-1-yl]-pyridin-3-yl}-amide, 4'-Cyano-6-methyl-biphenyl-3-carboxylic acid [6-(4-quinolin-5-ylmethyl-piperazin-1-yl)-pyridin-3-yl]-amide, 4'-Cyano-6-methyl-biphenyl-3-carboxylic acid [6-(4-pyridin-4-ylmethyl-piperazin-1-yl)-pyridin-3-yl]-amide, 4'-Cyano-6-methyl-biphenyl-3-carboxylic acid [6-(4-pyridin-2-ylmethyl-piperazin-1-yl)-pyridin-3-yl]-amide, 4'-Cyano-6-methyl-biphenyl-3-carboxylic acid {6-[4-(4-imidazol-1-yl-benzyl)-piperazin-1-yl]-pyridin-3-yl}-amide, 4'-Cyano-6-methylbiphenyl-3-carboxylic acid {6-[4-(3-cyano-benzyl)-piperazin-1-yl]-pyridin-3-yl}-amide, 4'-Cyano-6-methyl-biphenyl-3-carboxylic acid [6-(4-isoquinolin-5-ylmethyl-piperazin-1-yl)-pyridin-3-yl]-amide, (R)-2-methyl-N-(6-(2-methylmorpholino)pyridin-3-yl)-4'-(trifluoromethoxy)biphenyl-3-carboxamide, 4'-cyano-2-methyl-N-(6-sulfonylmorpholinopyridin-3-yl)biphenyl-3-carboxamide, (S)-4'-cyano-2-methyl-N-(6-(2-methylmorpholino)pyridin-3-yl)biphenyl-3-carboxamide, (R)-6-chloro-N-(6-(2-methylmorpholino)pyridin-3-yl)-4'-(trifluoromethoxy)biphenyl-3-carboxamide, 4'-cyano-2-methyl-N-(6-sulfinylmorpholinopyridin-3-yl)biphenyl-3-carboxamide, 4'-cyano-N-(6-(diisobutylamino)pyridin-3-yl)-2-methylbiphenyl-3-carboxamide, 4'-cyano-N-(2-((2S,6R)-2,6-dimethylmorpholino)pyrimidin-5-yl)-2-methylbiphenyl-3-carboxamide, N-(2-((2S,6R)-2,6-dimethylmorpholino)pyrimidin-5-yl)-2-methyl-4'-(trifluoromethyl)biphenyl-3-carboxamide, N-(2-((2S,6R)-2,6-dimethylmorpholino)pyrimidin-5-yl)-2-methyl-4'-(trifluoromethoxy)biphenyl-3-carboxamide, N-(2-(bis(2-hydroxyethyl)amino)pyrimidin-5-yl)-2-methyl-4'-(trifluoromethoxy)biphenyl-3-carboxamide, 2-methyl-N-(6-(tetrahydro-2H-pyran-4-yloxy)pyridin-3-yl)-4'-(trifluoromethoxy)biphenyl-3-carboxamide, N-(5-chloro-6-((2S,6R)-2,6-dimethylmorpholino)pyridin-3-yl)-2-methyl-4'-(trifluoromethoxy)biphenyl-3-carboxamide, N-(6-((2R,6S)-2,6-dimethyltetrahydro-2H-pyran-4-yl)pyridin-3-yl)-2-methyl-4'-(trifluoromethoxy)biphenyl-3-carboxamide, N-(6-(4-ethylpiperazine-1-carbonyl)pyridin-3-yl)-2-methyl-4'-(trifluoromethoxy)biphenyl-3-carboxamide, 2-methyl-N-(6-(2-oxopiperazin-1-yl)pyridin-3-yl)-4'-(trifluoromethoxy)biphenyl-3-carboxamide, 2-methyl-N-(6-(1-(pyridin-4-ylmethyl)piperidin-4-yl)pyridin-3-yl)-4'-(trifluoromethoxy)biphenyl-3-carboxamide, 2-methyl-N-(6-(2-oxo-4-(pyridin-4-ylmethyl)piperazin-1-yl)pyridin-3-yl)-4'-(trifluoromethoxy)biphenyl-3-carboxamide, 2-methyl-N-(6-(1-(pyridin-4-ylmethyl)piperidin-3-yl)pyridin-3-yl)-4'-(trifluoromethoxy)biphenyl-3-carboxamide, N-(6-(1-ethylpiperidin-3-yl)pyridin-3-yl)-2-methyl-4'-(trifluoromethoxy)biphenyl-3-carboxamide and N-(6-((2R,6S)-2,6-dimethylmorpholino)pyridin-3-yl)-2-methyl-4'-(trifluoromethoxy)biphenyl-3-carboxamide.

It is, therefore, specifically contemplated that compounds of Formula I which interfere with aspects of hedgehog, Ptc, or smoothened signal transduction activity will likewise be capable of inhibiting proliferation (or other biological consequences) in normal cells and/or cells having a patched loss-of-function phenotype, a hedgehog gain-of-function phenotype, a smoothened gain-of-function phenotype, a Gli gain-of-function phenotype, or an over expression of hedgehog ligands phenotype. Thus, it is contemplated that in certain embodiments, these compounds may be useful for inhibiting hedgehog activity in normal cells, e.g., which do not have a genetic mutation that activates the hedgehog pathway. In preferred embodiments, the compounds are capable of inhibiting at least some of the biological activities of hedgehog proteins, preferably specifically in target cells.

Thus, the methods of the present invention include the use of compounds of Formula I which agonize Ptc inhibition of hedgehog signaling, such as by inhibiting activation of smoothened or downstream components of the signal pathway, in the regulation of repair and/or functional performance of a wide range of cells, tissues and organs, including normal cells, tissues, and organs, as well as those having the phenotype of Ptc loss-of-function, hedgehog gain-of-function, smoothened gain-of-function or Gli gain-of-function. For instance, the subject method has therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Moreover, the subject methods can be performed on cells which are provided in culture (in vitro), or on cells in a whole animal (in vivo).

In another embodiment, the subject method can be to treat epithelial cells having a phenotype of Ptc loss-of-function, hedgehog gain-of-function, smoothened gain-of-function or Gli gain-of-function. For instance, the subject method can be used in treating or preventing basal cell carcinoma or other hedgehog pathway-related disorders.

In certain embodiments, a compound of Formula I can inhibit activation of a hedgehog pathway by binding to smoothened or its downstream proteins. In certain embodiments, a subject antagonist may inhibit activation of a hedgehog pathway by binding to patched.

In another preferred embodiment, the subject method can be used as part of a treatment regimen for malignant medulloblastomas and other primary CNS malignant neuroectodermal tumors.

In another aspect, the present invention provides pharmaceutical preparations comprising, as an active ingredient, a hedgehog signaling modulator such as a compound of Formula I, a Ptc agonist, a smoothened antagonist, or downstream hedgehog pathway protein antagonist such as described herein, formulated in an amount sufficient to inhibit, in vivo, proliferation or other biological consequences of Ptc loss-of-function, hedgehog gain-of-function, smoothened gain-of-function or Gli gain-of-function.

The subject treatments using a compound of Formula I, patched agonists, smoothened antagonists, or downstream hedgehog pathway protein antagonists can be effective for both human and animal subjects. Animal subjects to which the invention is applicable extend to both domestic animals and livestock, raised either as pets or for commercial purposes. Examples are dogs, cats, cattle, horses, sheep, hogs, and goats.

Pharmacology and Utility

The present invention makes available methods and compounds for inhibiting activation of the hedgehog signaling pathway, e.g., to inhibit aberrant growth states resulting from phenotypes such as Ptc loss-of-function, hedgehog gain-of-function, smoothened gain-of-function or Gli gain-of-function, comprising contacting the cell with a compound of Formula I, in a sufficient amount to agonize a normal Ptc activity, antagonize a normal hedgehog activity, antagonize smoothened activity, or antagonize Gli activity e.g., to reverse or control the aberrant growth state.

Members of the Hedgehog family of signaling molecules mediate many important short- and long-range patterning processes during vertebrate development. Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation. The effects of developmental cell interactions are varied: responding cells are diverted from one route of cell differentiation to another by inducing cells that differ from both the uninduced and induced states of the responding cells (inductions). Sometimes cells induce their neighbors to differentiate like themselves (homeogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation.

The vertebrate family of hedgehog genes includes three members that exist in mammals, known as Desert (Dhh), Sonic (Shh) and Indian (Ihh) hedgehogs, all of which encode secreted proteins. These various Hedgehog proteins consist of a signal peptide, a highly conserved N-terminal region, and a more divergent C-terminal domain. Biochemical studies have shown that autoproteolytic cleavage of the Hh precursor protein proceeds through an internal thioester intermediate which subsequently is cleaved in a nucleophilic substitution. It is likely that the nucleophile is a small lipophilic molecule which becomes covalently bound to the C-terminal end of the N-peptide, tethering it to the cell surface. The biological implications are profound. As a result of the tethering, a high local concentration of N-terminal Hedgehog peptide is generated on the surface of the Hedgehog producing cells. It is this N-terminal peptide which is both necessary and sufficient for short- and long-range Hedgehog signaling activities.

An inactive Hedgehog signaling pathway is where the transmembrane protein receptor Patched (Ptc) inhibits the activity of Smoothened (Smo), a seven transmembrane protein. The transcription factor Gli, a downstream component of Hh signaling, is prevented from entering the nucleus through interactions with cytoplasmic proteins, including Fused and Suppressor of fused (Sufu). As a consequence, transcriptional activation of Hedgehog target genes is repressed. Activation of the pathway is initiated through binding of any of the three mammalian ligands (Dhh, Shh or Ihh) to Ptc. Ligand binding results in a reversal of the repression of Smo, thereby activating a cascade that leads to the translocation of the active form of the transcription factor Gli to the nucleus. Nuclear Gli activates target gene expression, including Ptc and Gli itself.

Increased levels of Hedgehog signaling are sufficient to initiate cancer formation and are required for tumor survival. These cancers include, but are not limited to, prostate cancer ("Hedgehog signalling in prostate regeneration, neoplasia and metastasis", Karhadkar S S, Bova G S, Abdallah N, Dhara S, Gardner D, Maitra A, Isaacs J T, Berman D M, Beachy P A., Nature. 2004 Oct. 7; 431(7009):707-12; "Inhibition of prostate cancer proliferation by interference with SONIC HEDGEHOG-GLI1 signaling", Sanchez P, Hernandez A M, Stecca B, Kahler A J, DeGueme A M, Barrett A, Beyna M, Datta M W, Datta S, Ruiz i Altaba A., Proc Natl Acad Sci USA. 2004 Aug. 24; 101(34):12561-6), ("Cytotoxic effects induced by a combination of cyclopamine and gefitinib, the selective hedgehog and epidermal growth factor receptor signaling inhibitors, in prostate cancer cells," Mimeault M, Moore E, Moniaux N, et al (2006), International Journal of Cancer; 118 (4):1022-31) breast cancer ("Hedgehog signaling pathway is a new therapeutic target for patients with breast cancer", Kubo M, Nakamura M, Tasaki A, Yamanaka N, Nakashima H, Nomura M, Kuroki S, Katano M., Cancer Res. 2004 Sep. 1; 64(17):6071-4), ("Hedgehog signaling and Bmi-1 regulate self-renewal of normal and malignant human mammary stem cells," Liu S, Dontu G, Mantle I D, et al (2006) Cancer Res; 66 (12):6063-71), ("Constitutive activation of smoothened (SMO) in mammary glands of transgenic mice leads to increased proliferation, altered differentiation and ductal dysplasia," Moraes R C, Zhang X M, Harrington N, et al (2007), Development; 134 (6):1231-42), medulloblastoma ("Medulloblastoma growth inhibition by hedgehog pathway blockade", Berman D M, Karhadkar S S, Hallahan A R, Pritchard J I, Eberhart C G, Watkins D N, Chen J K, Cooper M K, Taipale J, Olson J M, Beachy P A., Science. 2002 Aug. 30; 297(5586):1559-61), non-melanoma skin cancer, i.e. squamous cell carcinoma (SCC) and basal cell carcinoma (BCC) ("Identification of a small molecule inhibitor of the hedgehog signaling pathway: effects on basal cell carcinoma-like lesions", Williams J A, Guicherit O M, Zaharian B I, Xu Y, Chai L, Wichterle H, Kon C, Gatchalian C, Porter J A, Rubin L L, Wang F Y., Proc Natl Acad Sci USA. 2003 Apr. 15; 100(8):4616-21; "Activating Smoothened mutations in sporadic basal-cell carcinoma", Xie J, Murone M, Luoh S M, Ryan A, Gu Q, Zhang C, Bonifas J M, Lam C W, Hynes M, Goddard A, Rosenthal A, Epstein E H Jr, de Sauvage F J., Nature. 1998 Jan. 1; 391(6662):90-2), pancreatic, esophagus, stomach, and billary cancers ("Hedgehog is an early and late mediator of pancreatic cancer tumorigenesis", Thayer S P, di Magliano M P, Heiser P W, Nielsen C M, Roberts D J, Lauwers G Y, Qi Y P, Gysin S, Fernandez-del Castillo C, Yajnik V, Antoniu B, McMahon M, Warshaw A L, Hebrok M., Nature. 2003 Oct. 23; 425(6960):851-6; "Widespread requirement for Hedgehog ligand stimulation in growth of digestive tract tumours", Berman D M, Karhadkar S S, Maitra A, Montes De Oca R, Gerstenblith M R, Briggs K, Parker A R, Shimada Y, Eshleman J R, Watkins D N, Beachy P A., Nature. 2003 Oct. 23; 425(6960):846-51), ("Nuclear factor-kappa B contributes to hedgehog signaling pathway activation through sonic hedgehog induction in pancreatic cancer," Nakashima H, Nakamura M, Yamaguchi H, et al (2006), Cancer Research; 66 (14):7041-9), ("Blockade of hedgehog signaling inhibits pancreatic cancer invasion and metastases: A new paradigm for combination therapy in solid cancers," Feldmann G, Dhara S, Fendrich V, et al (2007) Cancer Research; 67 (5): 2187-96), ("Oncogenic KRAS suppresses Gli1 degradation and activates Hedgehog signaling pathway in pancreatic cancer cells," Ji Z, Mei F C, Xie J, et al (2007), J Biol Chem; 282 (19):14048-55), and small-cell lung cancer ("Hedgehog signalling within airway epithelial progenitors and in small-cell lung cancer", Watkins D N, Berman D M, Burkholder S G, Wang B, Beachy P A, Baylin S B., Nature. 2003 Mar. 20; 422(6929):313-7), ("Hedgehog signaling in small-cell lung cancer: Frequent in vivo but a rare event in vitro," Vestergaard J, Pedersen M W, Pedersen N, et al (2006), Lung Cancer; 52 (3):281-90).

Additional cancers in which increased levels of Hedgehog signaling are sufficient to initiate cancer formation and are required for tumor survival include, but are not limited to colon cancer ("Sonic Hedgehog-dependent proliferation in a series of patients with colorectal cancer," Douard R, Moutereau S, Pernet P, et al (2006) Surgery; 139 (5):665-70), ("Hedgehog signalling in colorectal tumour cells: Induction of apoptosis with cyclopamine treatment," Qualtrough D, Buda A, Gaffield W, et al (2004), International Journal of Cancer; 110 (6):831-7), glioma, ("Cyclopamine-mediated Hedgehog pathway inhibition depletes stem-like cancer cells in glioblastoma," Bar E E, Chaudhry A, Lin A, et al, Neuro-Oncology; 2007, 9 (4):594), ("HEDGEHOG-GLI1 signaling regulates human glioma growth, cancer stem cell self-renewal, and tumorigenicity," Clement V, Sanchez P, de Tribolet N, et al, (2007) Current Biology 17 (2):165-72), ("Ligand-dependent activation of the hedgehog pathway in glioma progenitor cells," Ehteshan M, Sarangi A, Valadez J G, et al (2007) Oncogene; Mar. 12, 2007, Epub ahead of print), melanoma ("Melanomas require HEDGEHOG-GLI signaling reaulated by interactions between GLI1 and the RAS-MEK/AKT pathways," Stecca B, Mas C, Clement V, et al (2007), Proceedings of the National Academy of Sciences of the United States of America; 104 (14):5895-900), non small cell lung cancer (NSCLC) ("Frequent requirement of hedgehog signaling in non-small cell lung carcinoma," Yuan Z, Goetz J A, Singh S, et al (2007), Oncogene; 26 (7):1046-55), ovarian, ("Hedgehog signal pathway is activated in ovarian carcinomas, correlating with cell proliferation: It's inhibition leads to growth suppression and apoptosis," Chen X J, Horiuchi A, Kikuchi N, et al, Cancer Science; (2007) 98 (1):68-76), liver ("Activation of the hedgehog pathway in human hepatocellular carcinomas," Huang S H, He J, Zhang X L, et al (2006), Carcinogenesis; 27 (7):1334-40), ("Dysregulation of the Hedgehog pathway in human hepatocarcinogenesis," Sicklick J K, Li Y X, Jayaraman A, et al (2006), Carcinogenesis; 27 (4):748-57), renal ("Clear cell sarcoma of the kidney: Up-regulation of neural markers with activation of the sonic hedgehog and Akt pathways," Cutcliffe C, Kersey D, Huang C C, et al (2005), Clinical Cancer Research; 11 (22):7986-94), Rhabdomyosarcoma, ("Rhabdomyosarcomas and radiation hypersensitivity in a mouse model of Gorlin syndrome," Hahn H, Wojnowski L, Zimmer A M, et al (1998), Nature Medicine; 4 (5):619-22), ("Deregulation of the hedgehog signalling pathway: a possible role for the PTCH and SUFU genes in human rhabdomyoma and rhabdomyosarcoma development," Tostar U, Malm C J, Meis-Kindblom J M, et al (2006), Journal of Pathology; 208 (1):17-25), and Chondrosarcoma ("Constitutive hedgehog signaling in chondrosarcoma up-regulates tumor cell proliferation," Tiet T D, Hopyan S, Nadesan P, et al (2006), American Journal of Pathology; 168 (1):321-30).

Hedgehog pathway inhibitors (e.g. cyclopamine) have been shown to be useful in the treatment of psoriasis ("Cyclopamine inhibiting hedgehog in the treatment of psoriasis" Cutis, 2006, 78(3):185-8; Br. J. Dermatology, 2006 April; 154(4):619-23, "Psoriatic skin expresses the transcription factor Gli1: possible contribution of decreased neurofibromin expression", Endo H, Momota Y, Oikawa A, Shinkai H.).

Malignant lymphoma (ML) involves the cells of the lymphatic system, and is the fifth most common cancer in the U.S. ML includes Hodgkin's disease, and non-Hodgkin's diseases which are a heterogeneous group of lymphoid proliferative diseases. Hodgkin's disease accounts for approximately 14% of all malignant lymphomas. The non-Hodgkin's lymphomas are a diverse group of malignancies that are predominately of B-cell origin. In the Working Formulation classification scheme, these lymphomas been divided into low-, intermediate-, and high-grade categories by virtue of their natural histories (see "The Non-Hodgkin's Lymphoma Pathologic Classification Project," Cancer 49:2112-2135, 1982). The low-grade lymphomas are indolent, with a median survival of 5 to 10 years (Horning and Rosenberg, N. Engl. J. Med. 311: 1471-1475, 1984). Although chemotherapy can induce remissions in the majority of indolent lymphomas, cures are rare and most patients eventually relapse, requiring further therapy. The intermediate- and high-grade lymphomas are more aggressive tumors, but they have a greater chance for cure with chemotherapy. However, a significant proportion of these patients will relapse and require further treatment.

Multiple myeloma (MM) is malignant tumor composed of plasma cells of the type normally found in the bone marrow. These malignant plasma cells accumulate in bone marrow and typically produce monoclonal IgG or IgA molecules. The malignant plasma cells home to and expand in the bone marrow causing anemia and immunosuppression due to loss of normal hematopoiesis. Individuals suffering from multiple myeloma often experience anemia, osteolytic lesions, renal failure, hypercalcemia, and recurrent bacterial infections. MM represents the second most common hematopoietic malignancy.

The present invention is predicated in part on the discoveries by the present inventors that lymphoma and multiple myeloma diseases are dependent on the hedgehog (Hh) signaling pathway using lymphoma and plasmacytoma cells isolated from transgenic Eµ-Myc mice and Cdkn2a knockout mice, and discovering that hedgehog ligands mediate the interaction between stroma and lymphoma cells. The same was found for lymphoma and multiple myeloma samples isolated from patient samples from the bone (multiple myeloma) or from lymph nodes, bone marrow or spleens from non-Hodgkin's lymphoma (NHL) patients and also for chronic lymphocytic leukemia (CLL) samples. In addition, it was found that inhibition of the Hh signaling pathway induces apoptosis of stroma dependent lymphoma cells, and that overexpression of hedgehog pathway members inhibit cyclopamine induced apoptosis of lymphoma cells in vitro. Further, the inventors found that treating mice with hedgehog pathway inhibitors abrogates lymphoma expansion in vivo. Finally, the inventors discovered that there is no expression of Gli3 in spleen B-cells and in the majority of cyclopamine responsive lymphomas, but a predominant expression in all cyclopamine resistant lymphomas.

These data indicate that Hh signaling provides an important anti-apoptotic signal for the initial steps of transformation by c-Myc and plays an important role for lymphoma maintenance Thus, disruption of the Hh signaling pathway provides novel means for treating lymphomas (e.g., NHL), multiple myelomas, CLL and other hematopoietic malignancies. In addition, expression of Gli3 in lymphomas provides a negative predictive factor for responsiveness to Hh inhibition and an important means for patient stratification.

In accordance with these discoveries, the invention provides methods for inhibiting growth of tumor cells, e.g., lymphoma and myeloma cells. The invention provides methods and compositions to treat lymphoma or myeloma in a subject by inhibiting growth of tumor cells. The methods are also useful to prevent tumorigenesis in a subject. Some of the methods are directed to treating lymphomas which do not have significant expression of Gli3 relative to spleen B cells. The methods involve administering to the subject in need of treatment a pharmaceutical composition that contains an antagonizing agent of Hh signaling (e.g., a compound of Formula I). Compound of the invention down-regulate cellular level or inhibit a biological activity of an Hh signaling pathway member.

This invention provides methods of prophylactic or therapeutic treatment of cancers of the blood and lymphatic systems, including lymphomas, leukemia, and myelomas. The methods employ an antagonist of hedgehog signaling pathway to inhibit growth and proliferation of lymphoma cells, leukemia cells, or myeloma cells. Lymphoma is malignant tumor of lymphoblasts derived from B lymphocytes. Myeloma is a malignant tumor composed of plasma cells of the type normally found in the bone marrow. Leukemia is an acute or chronic disease that involves the blood forming organs. NHLs are characterized by an abnormal increase in the number of leucocytes in the tissues of the body with or without a corresponding increase of those in the circulating blood and are classified according to the type of leucocyte most prominently involved.

By way of example, subjects suffering from or at risk of development of lymphoma (e.g., e.g., B-cell lymphoma, plasmoblastoma, plasmacytoma or CLL) can be treated with methods of the invention. Preferably, the subject is a human being. The methods entail administering to the subject a pharmaceutical composition containing an effective amount of a compound of Formula I to inhibit the hedgehog signaling pathway. The subject can be one who is diagnosed with lymphoma, with or without metastasis, at any stage of the disease (e.g., stage I to IV, Ann Arbor Staging System). Lymphomas suitable for treatment with methods of the invention include but are not limited to Hodgkin's disease and non-Hodgkin's disease. Hodgkin's disease is a human malignant disorder of lymph tissue (lymphoma) that appears to originate in a particular lymph node and later spreads to the spleen, liver and bone marrow. It occurs mostly in individuals between the ages of 15 and 35. It is characterized by progressive, painless enlargement of the lymph nodes, spleen and general lymph tissue. Classic Hodgkin's disease is divided into four subtypes: (1) nodular sclerosis Hodgkin's disease (NSHD); (2) mixed cellularity Hodgkin's disease (MCHD); (3) lymphocyte depletion Hodgkin's disease (LDHD); and (4) lymphocyte-rich classic Hodgkin's disease (cLRHD).

In some preferred embodiments, the present methods are used to treat non-Hodgkin's Lymphoma (NHL). Non-Hodgkin's disease is also called lymphosarcoma and refers to a group of lymphomas which differ in important ways from Hodgkin's disease and are classified according to the microscopic appearance of the cancer cells. Non-Hodgkin's lymphoma includes but is not limited to (1) slow-growing lymphomas and lymphoid leukemia (e.g., chronic lymphocytic leukemia, small lymphocytic leukemia, lymphoplasmacytoid lymphoma, follicle center lymphoma, follicular small cleaved cell, follicular mixed cell, marginal zone B-cell lymphoma, hairy cell leukemia, plasmacytoma, myeloma, large granular lymphocyte leukemia, mycosis fungoides, szary syndrome); (2) moderately aggressive lymphomas and lymphoid leukemia (e.g., prolymphocytic leukemia, mantle cell lymphoma, follicle center lymphoma, follicular small cleaved cell, follicle center lymphoma, chronic lymphocytic leukemia/prolymphocytic leukemia, angiocentric lymphoma, angioimmunoblastic lymphoma); (3) aggressive lymphomas (e.g., large B-cell lymphoma, peripheral T-cell lymphomas, intestinal T-cell lymphoma, anaplastic large cell lymphoma); and (4) highly aggressive lymphomas and lymphoid leukemia (e.g., B-cell precursor B-lymphoblastic leukemia/lymphoma, Burkitt's lymphoma, high-grade B-cell lymphoma, Burkitt's-like T-cell precursor T-lymphoblastic leukemia/lymphoma). The methods of the present invention can be used for adult or childhood forms of lymphoma, as well as lymphomas at any stage, e.g., stage I, II, III, or IV. The methods described herein can also be employed to treat other forms of leukemia, e.g., acute lymphocytic leukemia (ALL).

Some of the therapeutic methods of the invention are particularly directed to treating lymphomas or myelomas which do not express Gli3. As disclosed in the Examples below, it was observed that, while Gli1 and Gli2 were expressed in all lymphomas, detectable Gli3 expression was present mainly in lymphomas which were resistant to Hh pathway inhibition by cyclopamine. There is no expression of Gli3 in normal spleen B-cells and in the majority of cyclopamine responsive lymphomas. Thus, prior to treatment with Hh antagonists, subjects with lymphomas can be first examined for expression of Gli3 in a lymphoma cell sample obtained from the subject. Gli3 expression level in the sample can be compared to Gli3 expression level in normal spleen B cells obtained from the subject. Gli3 expression levels in the lymphoma or myeloma samples and the control cells can be determined using methods well known in the art, e.g., as described in the Examples below. A likely responsiveness to treatment with Hh antagonists described herein is indicated by the lack of detectable Gli3 expression in the lymphoma or myeloma samples or an expression level that is not significantly higher (e.g., not more than 25%, 50%, or 100% higher) than Gli3 expression level in the normal B cell. Other than being an additional step of the therapeutic methods of the invention, the pre-screening for lack of Gli3 expression can be used independently as a method for patient stratification.

In addition to lymphomas, the methods and compositions described above are also suitable for the treatment of myelomas. Multiple myeloma is a fatal neoplasm characterized by an accumulation of a clone of plasma cells, frequently accompanied by the secretion of Ig chains. Bone marrow invasion by the tumor is associated with anemia, hypogammaglobinemia, and granulocytopenia with concomitant bacterial infections. An abnormal cytokine environment, principally raised IL-6 and IL-1β levels, often results in increased osteoclasis leading to bone pain, fractures, and hypercalcemia. Despite aggressive chemotherapy and transplantation, multiple myeloma is a universally fatal plasma proliferative disorder.

Compounds of the invention are useful in the treatment of hedgehog related disorders such as basal cell nevus syndrome (also called Gorlin's syndrome and/or nevoid basal cell carcinoma), a rare autosomal dominant cancer genetic syndrome.

Compounds of the invention are useful in the treatment of basal cell carcinoma (BCC or rodent ulcer), tumors of the adrenal glands arising from the cortex or the medulla part of the adrenal gland medulla, and ovarian tumors.

Compounds of the invention are useful in the treatment of bone overgrowth disorders including, but are not limited to, acromegaly, macrocephaly, Sotos syndrome, progressive diaphyseal dysplasia (PDD or Camurati-Engelmann disease), craniodiaphyseal dysplasia, and endosteal hyperostosis disorders including Van Buchem disease (types I and II) and sclerosteosis.

Compounds of the invention are useful in the treatment of unwanted hair growth, for example, hairy moles and cosmetic prevention of hair regrowth after epilation.

Compounds of the invention are useful in the treatment of Liver fibrosis.

Thus, the methods of the present invention include the use of compounds of the invention which agonize Ptc inhibition of Hedgehog signaling, such as by inhibiting activation of smoothened or downstream components of the signal pathway, in the regulation of repair and/or functional performance of a wide range of cells, tissues and organs, including normal cells, tissues, and organs, as well as those having the phenotype of Ptc loss-of-function, Hedgehog gain-of-function, smoothened gain-of-function or Gli gain-of-function. For instance, the subject method has therapeutic and cosmetic applications ranging from regulation of neural tissues, bone and cartilage formation and repair, regulation of spermatogenesis, regulation of benign prostate hyperplasia, regulation of blood vessel formation in wet macular degeneration, psoriasis, regulation of smooth muscle, regulation of lung, liver and other organs arising from the primitive gut, regulation of hematopoietic function, regulation of skin and hair growth, etc. Moreover, the subject methods can be performed on cells which are provided in culture (in vitro), or on cells in a whole animal (in vivo).

In accordance with the foregoing, the present invention further provides a method for preventing or treating any of the diseases or disorders described above in a subject in need of such treatment, which method comprises administering to said subject a therapeutically effective amount (See, "Administration and Pharmaceutical Compositions", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions:

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with other therapies, such as radiation therapy, bone marrow transplantation or hormone therapy.

Compounds of the invention can be administered in therapeutically effective amounts in combination with one or more therapeutic agents (pharmaceutical combinations). For example, synergistic effects can occur with immunomodulatory, anti-inflammatory substances, other anti-tumor therapeutic agents, chemotherapeutic agents, ablation or other therapeutic hormones, antineoplastic agents and/or monoclonal antibodies useful against lymphomas or myelomas. Some of the well known anti-cancer drugs are described in the art, e.g., *Cancer Therapeutics: Experimental and Clinical Agents*, Teicher (Ed.), Humana Press ($1^{st}$ ed., 1997); and *Goodman and Gilman's The Pharmacological Basis of Therapeutics*, Hardman et al. (Eds.), McGraw-Hill Professional ($10^{th}$ ed., 2001). Examples of suitable anti-cancer drugs include 5-fluorouracil, vinblastine sulfate, estramustine phosphate, suramin and strontium-89. Examples of suitable chemotherapeutic agents include Asparaginase, Bleomycin Sulfate, Cisplatin, Cytarabine, Fludarabine Phosphate, Mitomycin and Streptozocin.

Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I can be prepared by proceeding as in the following Reaction Scheme I:

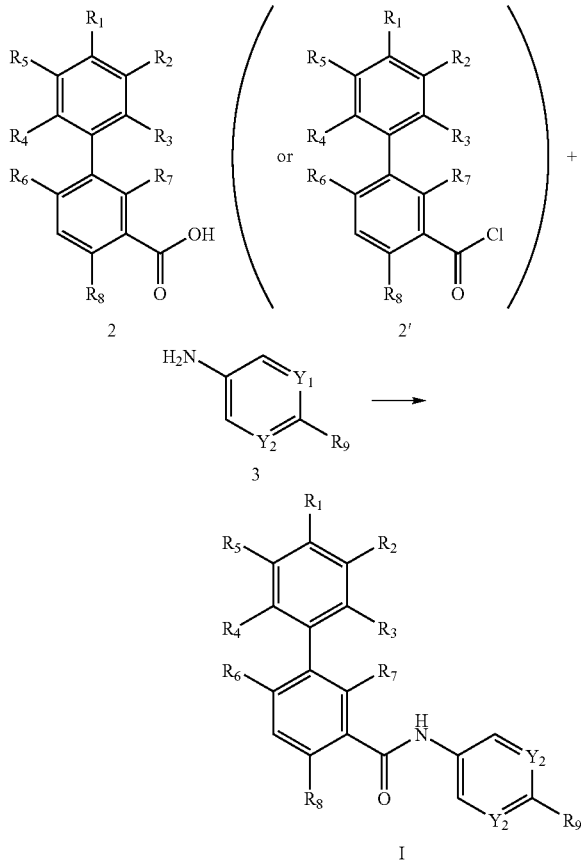

in which $Y_1$, $Y_2$, $R_1$, $R_2$, $R_3$, $R_4$, $R_5$, $R_6$, $R_7$, $R_8$ and $R_9$ are as defined for Formula I in the Summary of the Invention. A compound of Formula I can be prepared by reacting a compound of formula 2 (or 2') with a compound of formula 3 in the presence of a suitable solvent (e.g., dichloromethane, N,N-dimethylformide or the like), in a temperature range of about −20 to about 100° C. The reaction can take up to about 20 hours to complete.

Detailed examples of the synthesis of compounds of Formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) those of reaction scheme I; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following example that illustrates the preparation of compounds of Formula I according to the invention.

Example 1

4'-cyano-6-methyl-biphenyl-3-carboxylic acid [4-(morpholine-4-sulfonyl)-phenyl]-amide

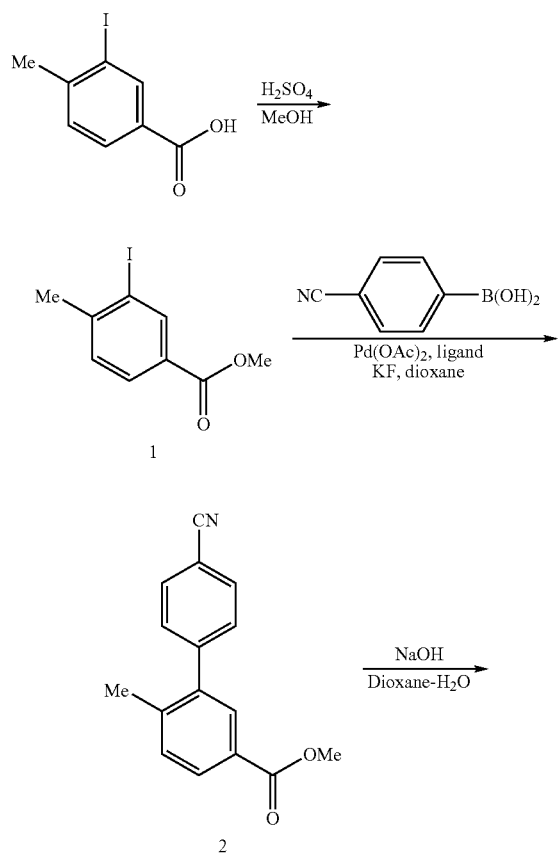

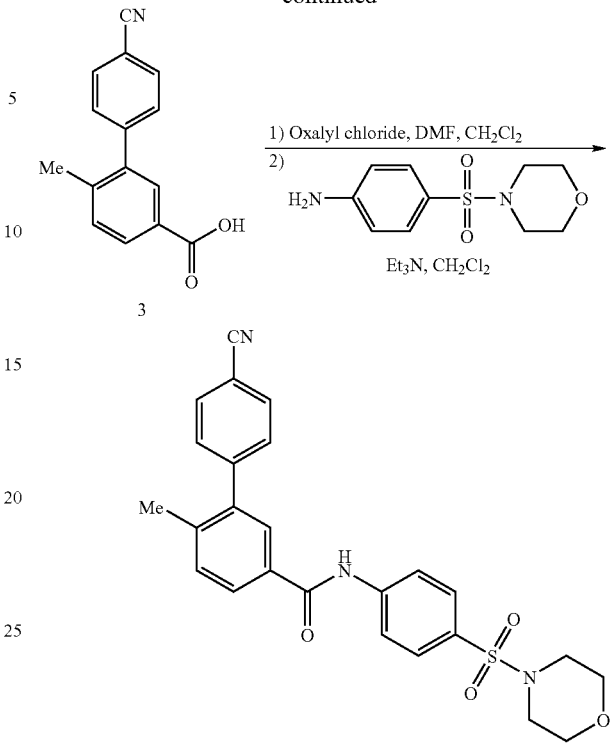

Example 1

Step 1: To a solution of 3-iodo-4-methyl-benzoic acid (10.0 g, 38.2 mmol) in methanol (70 ml) is added concentrated sulfuric acid (0.5 ml). The reaction mixture is heated at 70° C. for 48 hours, cooled to room ambient temperature and then concentrated. After that, ethyl acetate (100 ml) and aqueous $NaHCO_3$ (saturated, 100 ml) solution are added to the residue. The organic layer is separated and washed again with aqueous $NaHCO_3$ (saturated, 100 ml) solution. The organic layer is separated, dried over anhydrous $Na_2SO_4$ and concentrated to yield 3-iodo-4-methyl-benzoic acid methyl ester 1. It is used without further purification in the next step. $^1$H NMR (400 MHz, DMSO-$d_6$) δ 8.31 (s, 1H), 7.87 (d, 1H, J=8.4 Hz), 7.48 (d, 1H, J=8.4 Hz), 3.85 (s, 3H), 3.35 (s, 3H); LC-MS m/z: 277.0 (M+1).

Step 2: To a round-bottom flask containing 3-iodo-4-methyl-benzoic acid methyl ester (1.38 g, 5.00 mmol), 4-cyanophenylboronic acid (1.10 g, 7.48 mmol), palladium acetate (168 mg, 0.748 mmol), 2-(dicyclohexylphosphino)biphenyl (0.526 g, 1.50 mmol) and potassium fluoride (0.870 g, 15.0 mmol) is added anhydrous 1,4-dioxane (15 ml). The flask is purged with argon and sealed. The mixture is stirred at 130° C. for 18 hours, cooled to ambient temperature and then water (20 ml) and ethyl acetate (20 ml) are added. Solid is removed under vacuum filtration. The filtrate is extracted with EtOAc (20 ml×2). The organic layers are combined, washed with aqueous HCl (5%, 20 ml) and saturated $NaHCO_3$ (20 ml). It is dried over $MgSO_4$, and concentrated. The residue is purified by silica gel column chromatography (EtOAc/Hexane, gradient) to give 4'-cyano-6-methyl-biphenyl-3-carboxylic acid methyl ester 2; LC-MS m/z: 252.1 (M+1).

Step 3: To a solution of 4'-cyano-6-methyl-biphenyl-3-carboxylic acid methyl ester 2 (2.56 g, 10.3 mmol) in 1,4-dioxane-$H_2O$ (1:1 mixture, 20 ml) is added NaOH (1.22 g, 30.2 mmol)). The reaction is stirred at ambient temperature for 24 hours. To this mixture is added aqueous HCl (1 N, 36 ml) and it is then extracted with ethyl acetate (40 ml×3). The organic layers are combined, dried over anhydrous $Na_2SO_4$. The solver is removed. The solid obtained is washed with small amount of acetonitrile and air dried to give 4'-cyano-6-methyl-biphenyl-3-carboxylic acid 3: $^1H$ NMR (DMSO-$d_6$) δ 7.94 (d, 2H, J=8.0 Hz), 7.84 (dd, 1H, $J_1$=8.4 Hz, $J_2$=1.2 Hz), 7.75 (d, 1H, J=1.2 Hz), 7.61 (d, 2H, J=8.0 Hz), 7.48 (d, 1H, J=8.4 Hz), 2.29 (s, 3H); LC-MS m/z 238.1 (M+1).

Step 4: To a suspension of 4'-cyano-6-methyl-biphenyl-3-carboxylic acid 3 (40 mg, 0.17 mmol) in anhydrous methylene chloride (5 ml) is added 2 drops of DMF. Then oxalyl chloride (32 mg, 22 μl, 0.25 mmol) is added. The mixture is stirred at ambient temperature until it turns clear. After that, it is concentrated, re-dissolved in anhydrous methylene chloride (3 ml), and added to a solution of 4-(morpholine-4-sulfonyl)-phenylamine (61 mg, 0.25 mmol) and triethylamine (34 mg, 47 μl, 0.33 mmol) in methylene chloride (2 ml). The mixture is stirred for 2 hours, concentrated and the residue is purified by preparative mass triggered HPLC ($C_{18}$ column, eluted with $CH_3CN$—$H_2O$ containing 0.05% TFA) to give 4'-cyano-6-methyl-biphenyl-3-carboxylic acid [4-(morpholine-4-sulfonyl)-phenyl]-amide: $^1H$ NMR (DMSO-$d_6$) δ 10.64 (s, 1H), 8.07 (d, 2H, J=8.8 Hz), 7.97 (d, 2H, J=8.4 Hz), 7.95 (d, 1H, J=8.8 Hz), 7.89 (s, 1H), 7.43 (d, 2H, J=8.4 Hz), 7.67 (d, 2H, J=8.8 Hz), 7.53 (d, 2H, J=8.8 Hz), 3.63 (m, 4H), 2.84 (m, 4H) 2.32 (s, 3H); LC-MS m/z: 462.1 (M+1).

Example 2

4'-cyano-6-methyl-biphenyl-3-carboxylic acid [6-(2,6-dimethyl-morpholin-4-yl)-pyridin-3-yl]-amide

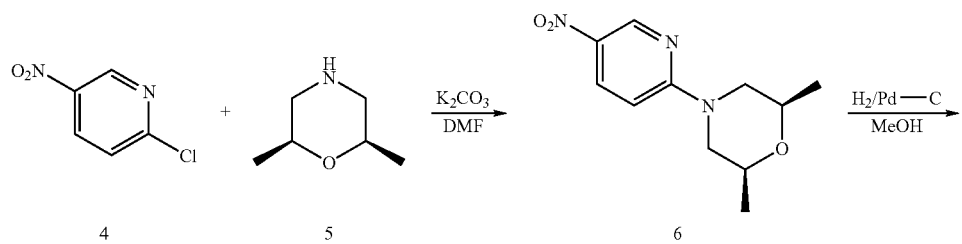

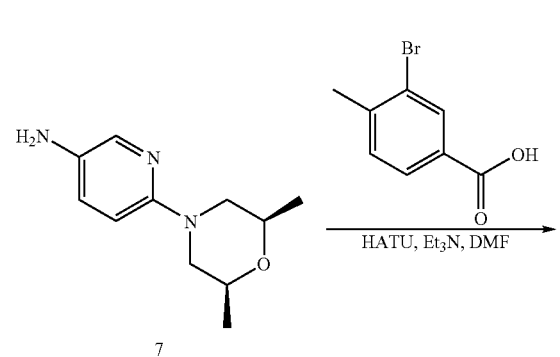

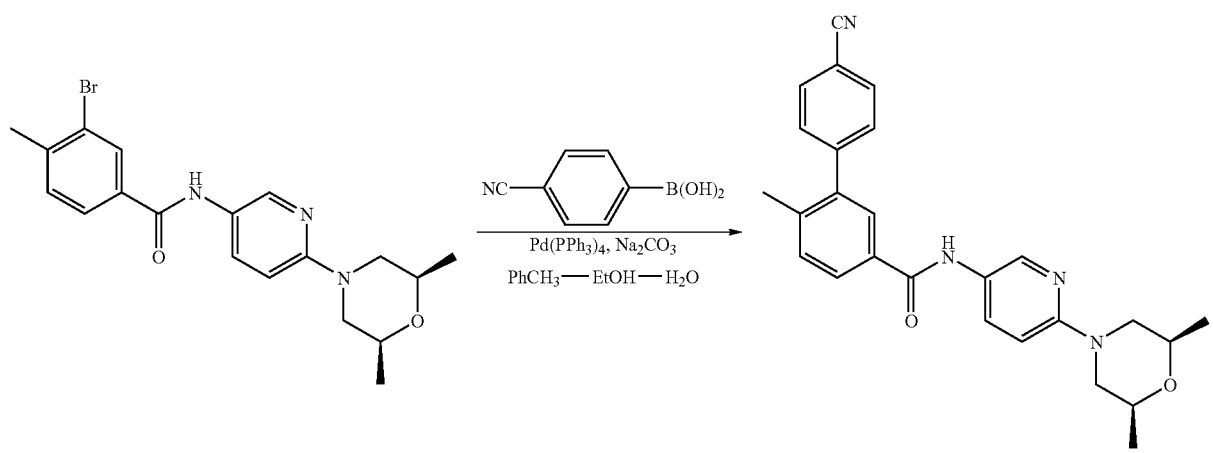

Step 1: To a solution of 2-chloro-5-nitro-pyridine 4 (2.38 g, 15 mmol.) and cis-2,6-dimethylmorpholine (1.73 g, 15 mmol.) is added $K_2CO_3$ (4.14 g, 30 mmol.). The mixture was heated at 50° C. overnight. After concentration, the residue is partitioned between EtOAc and water. The EtOAc layer is dried over anhydrous $Na_2SO_4$ and concentrated to give crude product 6 as a yellow solid. The crude product is used directly in next step without further purification. LC-MS m/z: 238.1 (M+1).

Step 2: The above crude material 6 is hydrogenated in the presence of Pd—C (0.2 g) in MeOH (100 mL) under hydrogen over 10 h. The suspension is filtered through celite and the filtrate is concentrated to give the crude product 7 as a dark brown oil which is used directly in the next step without further purification. LC-MS m/z: 208.1 (M+1).

Step 3: To a solution of 3-bromo-4-methyl benzoic acid (108 mg, 0.5 mmol.), 6-(2,6-Dimethyl-morpholin-4-yl)-pyridin-3-ylamine 7 (104 mg, 0.5 mmoL), and HATU (190 mg, 0.5 mmol.) in dry DMF (5 mL) is added triethylamine (139 uL, 1.0 mmol.) dropwise. The resulting mixture is stirred at room temperature for 2 h. After concentration, the residue is partitioned between EtOAc and water. The organic layer is dried and concentrated to give the crude product. The final compound is purified by flash column chromatography using 50% EtOAc in hexane as eluent to give 8 as a white solid. LC-MS m/z: 404.1 (M+1).

Step 4: A mixture of 4-cyanophenyl boronic acid (18 mg, 0.12 mmol), 3-bromo-N-[6-(2,6-dimethyl-morpholin-4-yl)-pyridin-3-yl]-4-methyl-benzamide 8 (40 mg, 0.1 mmol), $Pd(PPh_3)_4$ (11 mg, 0.01 mmol), and $Na_2CO_3$ (42 mg, 0.4 mmol) in a combined solvent system of toluene (0.2 mL) and water (0.2 mL) and ethanol (0.05 mL) is heated at 140° C. under microwave irradiation for 30 min. The reaction mixture is diluted with EtOAc and water. The aqueous layer is extracted with EtOAc. The combined organic layer is washed with brine and concentrated to give the crude product which is purified by preparative mass triggered HPLC ($C_{18}$ column, eluted with $CH_3CN$—$H_2O$ containing 0.05% TFA) to give 4'-cyano-6-methyl-biphenyl-3-carboxylic acid [6-(2,6-dimethyl-morpholin-4-yl)-pyridin-3-yl]-amide. LC-MS m/z: 427.2 (M+1).

By repeating the procedures described in the above examples, using appropriate starting materials, the following compounds of Formula I, as identified in Table 1, are obtained.

TABLE 1

| Compound Number | Structure | Physical Data MS (m/z) |
| --- | --- | --- |
| 3 | 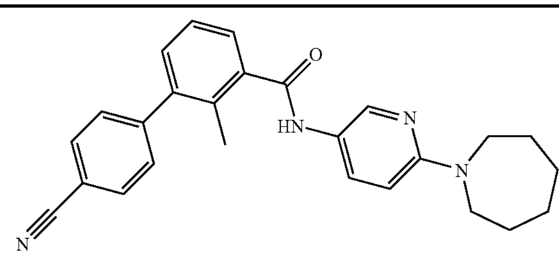 | LC-MS m/z 411.2 (M + 1). |
| 4 | 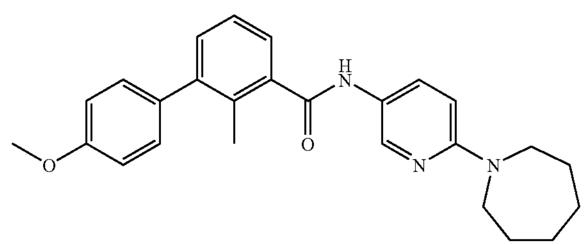 [SMILES: COc1ccc(-c2cccc(C(=O)Nc3ccc(N4CCCCCC4)nc3)c2C)cc1] | LC-MS m/z 416.2 (M + 1). |
| 5 | 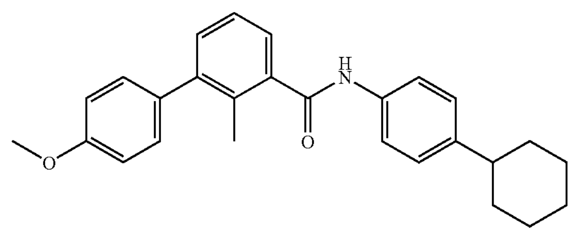 [SMILES: COc1ccc(-c2cccc(C(=O)Nc3ccc(C4CCCCC4)cc3)c2C)cc1] | LC-MS m/z 400.2 (M + 1). |
| 6 | 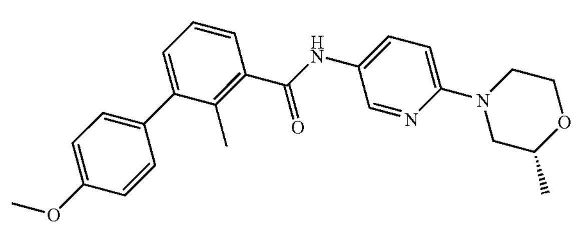 [SMILES: COc1ccc(-c2cccc(C(=O)Nc3ccc(N4CCO[C@H](C)C4)nc3)c2C)cc1] | LC-MS m/z 418.2 (M + 1). |

TABLE 1-continued

| Compound Number | Structure | Physical Data MS (m/z) |
|---|---|---|
| 7 | 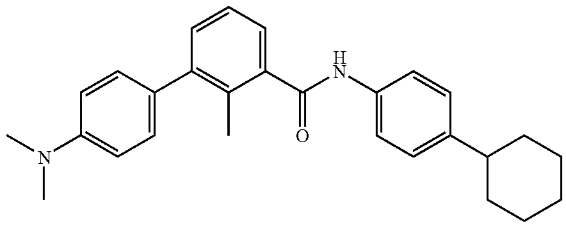 [SMILES: Cc1c(C(=O)Nc2ccc(C3CCCCC3)cc2)cccc1-c1ccc(N(C)C)cc1] | LC-MS m/z 413.2 (M + 1). |
| 8 | 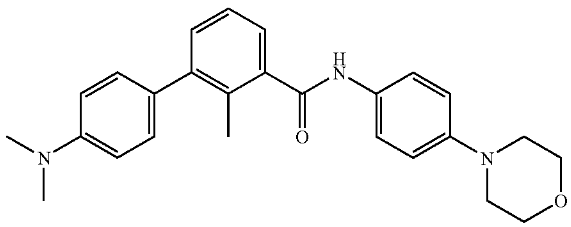 [SMILES: Cc1c(C(=O)Nc2ccc(N3CCOCC3)cc2)cccc1-c1ccc(N(C)C)cc1] | LC-MS m/z 416.2 (M + 1). |
| 9 | 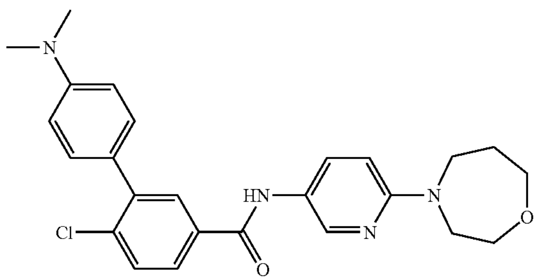 [SMILES: CN(C)c1ccc(-c2cc(C(=O)Nc3ccc(N4CCCOCC4)nc3)ccc2Cl)cc1] | LC-MS m/z 451.2 (M + 1). |
| 10 | 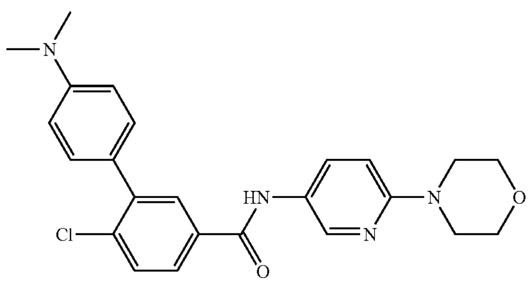 [SMILES: CN(C)c1ccc(-c2cc(C(=O)Nc3ccc(N4CCOCC4)nc3)ccc2Cl)cc1] | LC-MS m/z 437.2 (M + 1). |
| 11 | 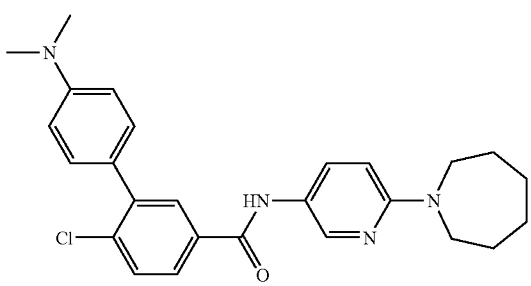 [SMILES: CN(C)c1ccc(-c2cc(C(=O)Nc3ccc(N4CCCCCC4)nc3)ccc2Cl)cc1] | LC-MS m/z 449.2 (M + 1). |
| 12 | 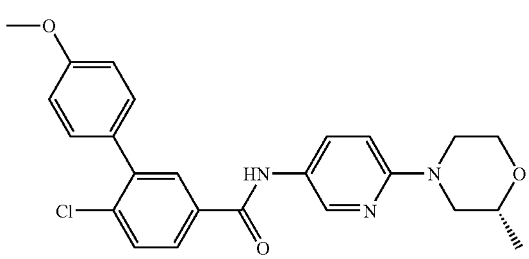 | LC-MS m/z 438.2 (M + 1). |

TABLE 1-continued

| Compound Number | Structure | Physical Data MS (m/z) |
|---|---|---|
| 13 | 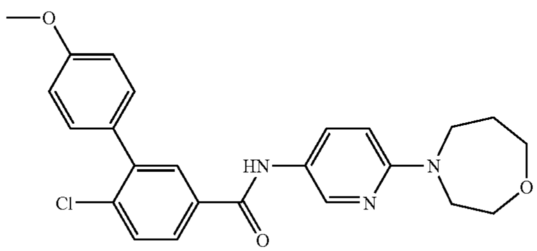 | LC-MS m/z 438.2 (M + 1). |
| 14 | 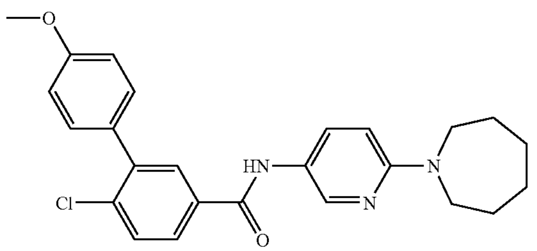 [SMILES: COc1ccc(-c2cc(C(=O)Nc3ccc(N4CCCCCC4)nc3)ccc2Cl)cc1] | LC-MS m/z 436.2 (M + 1). |
| 15 | 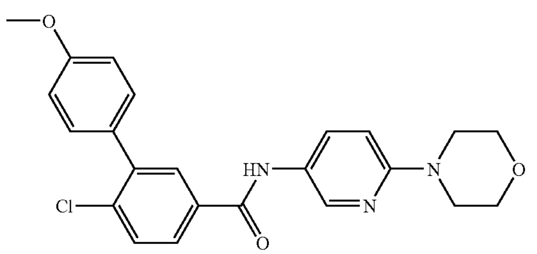 [SMILES: COc1ccc(-c2cc(C(=O)Nc3ccc(N4CCOCC4)nc3)ccc2Cl)cc1] | LC-MS m/z 424.1 (M + 1). |
| 16 | 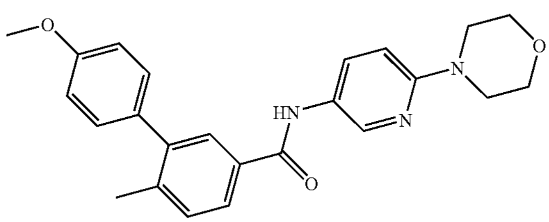 [SMILES: COc1ccc(-c2cc(C(=O)Nc3ccc(N4CCOCC4)nc3)ccc2C)cc1] | LC-MS m/z 404.2 (M + 1). |
| 17 | 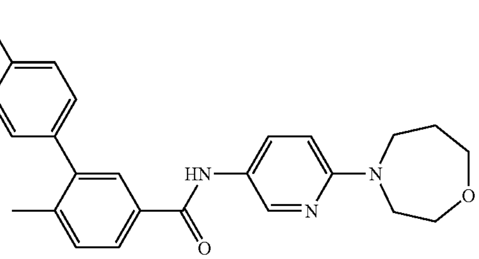 | LC-MS m/z 418.2 (M + 1). |
| 18 | 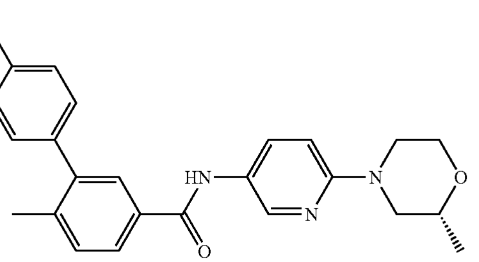 | LC-MS m/z 418.2 (M + 1). |

TABLE 1-continued

| Compound Number | Structure | Physical Data MS (m/z) |
|---|---|---|
| 19 | 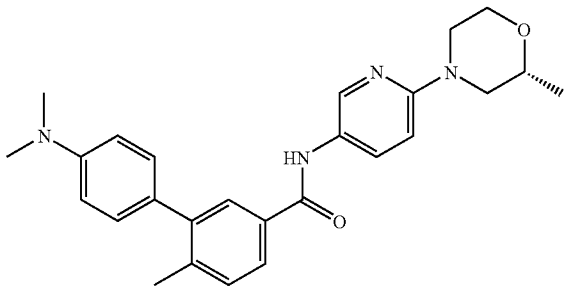 | LC-MS m/z 431.2 (M + 1). |
| 20 | 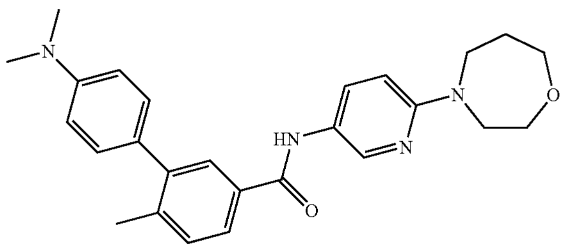 [SMILES: Cc1ccc(C(=O)Nc2ccc(N3CCCOCC3)nc2)cc1-c1ccc(N(C)C)cc1] | LC-MS m/z 431.2 (M + 1). |
| 21 | 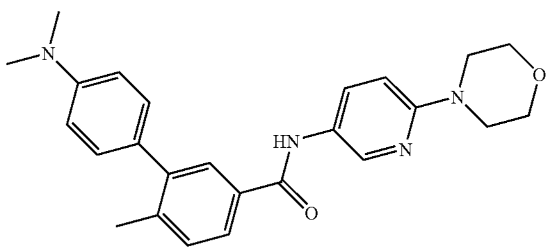 [SMILES: Cc1ccc(C(=O)Nc2ccc(N3CCOCC3)nc2)cc1-c1ccc(N(C)C)cc1] | LC-MS m/z 417.2 (M + 1). |
| 22 | 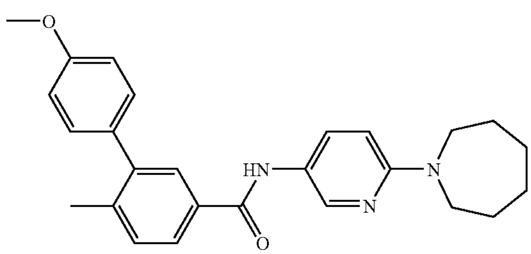 | LC-MS m/z 416.2 (M + 1). |
| 23 | 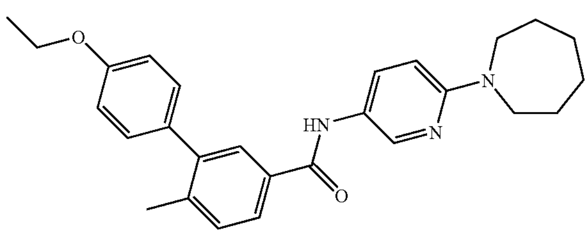 [SMILES: CCOc1ccc(-c2cc(C(=O)Nc3ccc(N4CCCCCC4)nc3)ccc2C)cc1] | LC-MS m/z 430.2 (M + 1). |
| 24 | 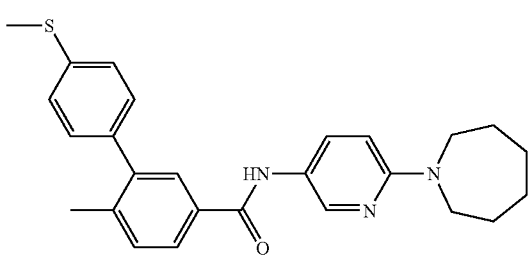 [SMILES: CSc1ccc(-c2cc(C(=O)Nc3ccc(N4CCCCCC4)nc3)ccc2C)cc1] | LC-MS m/z 432.2 (M + 1). |

TABLE 1-continued

| Compound Number | Structure | Physical Data MS (m/z) |
|---|---|---|
| 25 | 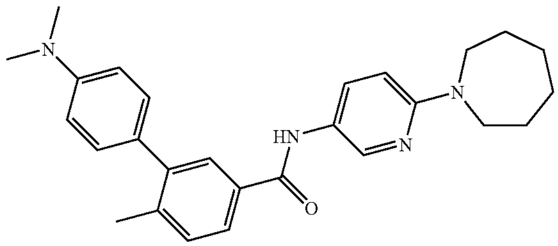 | LC-MS m/z 429.2 (M + 1). |
| 26 | 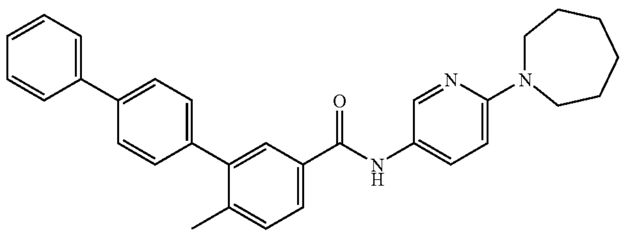 [SMILES: Cc1ccc(C(=O)Nc2ccc(N3CCCCCC3)nc2)cc1-c1ccc(-c2ccccc2)cc1] | LC-MS m/z 462.2 (M + 1). |
| 27 | 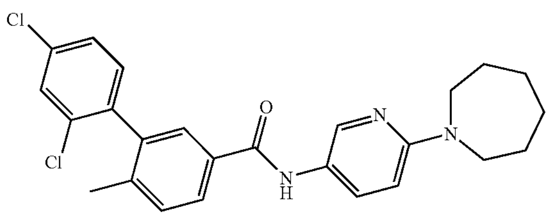 [SMILES: Cc1ccc(C(=O)Nc2ccc(N3CCCCCC3)nc2)cc1-c1ccc(Cl)cc1Cl] | LC-MS m/z 454.1 (M + 1). |
| 28 | 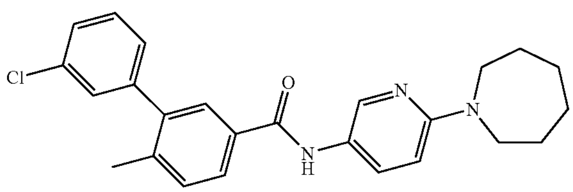 [SMILES: Cc1ccc(C(=O)Nc2ccc(N3CCCCCC3)nc2)cc1-c1cccc(Cl)c1] | LC-MS m/z 420.2 (M + 1). |
| 29 | 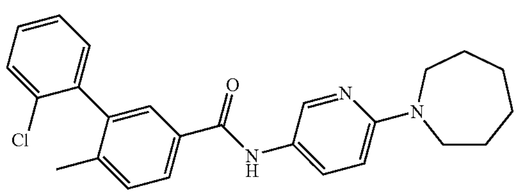 [SMILES: Cc1ccc(C(=O)Nc2ccc(N3CCCCCC3)nc2)cc1-c1ccccc1Cl] | LC-MS m/z 420.2 (M + 1). |
| 30 | 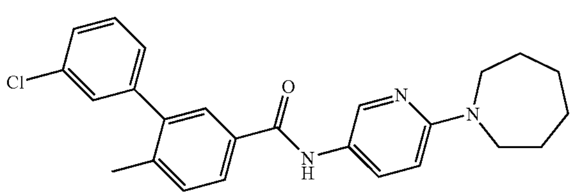 [SMILES: Cc1ccc(C(=O)Nc2ccc(N3CCCCCC3)nc2)cc1-c1cccc(Cl)c1] | LC-MS m/z 420.2 (M + 1). |
| 31 | 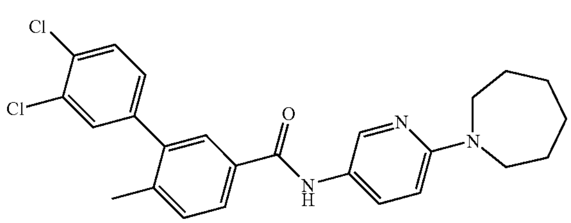 [SMILES: Cc1ccc(C(=O)Nc2ccc(N3CCCCCC3)nc2)cc1-c1ccc(Cl)c(Cl)c1] | LC-MS m/z 454.2 (M + 1). |

TABLE 1-continued
| Compound Number | Structure | Physical Data MS (m/z) |
|---|---|---|
| 32 | 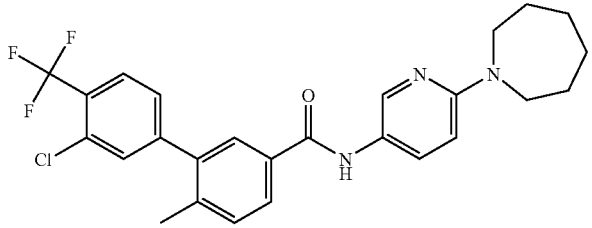 [SMILES: Cc1ccc(C(=O)Nc2ccc(N3CCCCCC3)nc2)cc1-c1ccc(C(F)(F)F)c(Cl)c1] | LC-MS m/z 488.1 (M + 1). |
| 33 | 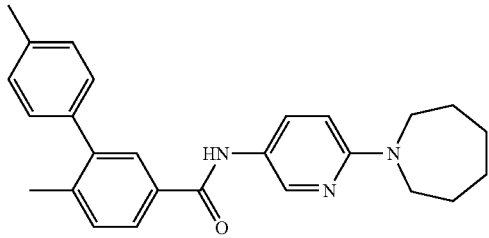 [SMILES: Cc1ccc(-c2cc(C(=O)Nc3ccc(N4CCCCCC4)nc3)ccc2C)cc1] | LC-MS m/z 400.2 (M + 1). |
| 34 | 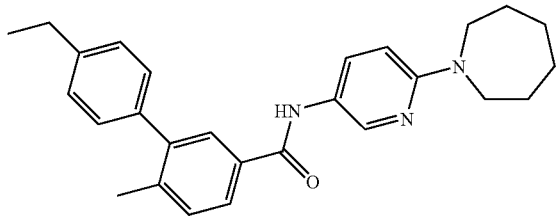 [SMILES: CCc1ccc(-c2cc(C(=O)Nc3ccc(N4CCCCCC4)nc3)ccc2C)cc1] | LC-MS m/z 414.2 (M + 1). |
| 35 | 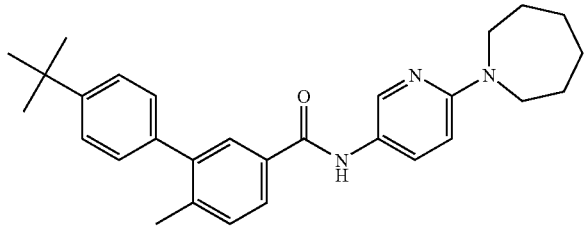 [SMILES: Cc1ccc(C(=O)Nc2ccc(N3CCCCCC3)nc2)cc1-c1ccc(C(C)(C)C)cc1] | LC-MS m/z 442.2 (M + 1). |
| 36 | 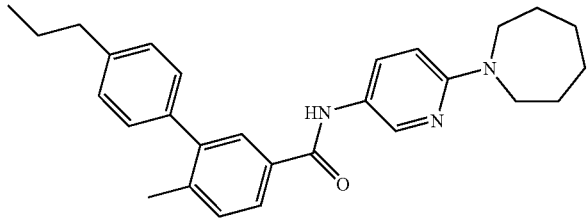 | LC-MS m/z 428.2 (M + 1). |
| 37 | 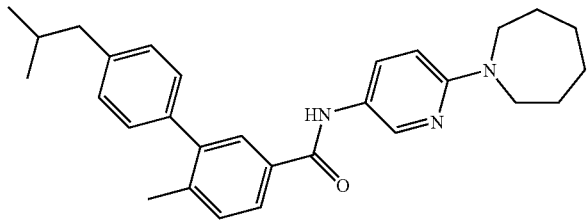 [SMILES: Cc1ccc(C(=O)Nc2ccc(N3CCCCCC3)nc2)cc1-c1ccc(CC(C)C)cc1] | LC-MS m/z 442.2 (M + 1). |

TABLE 1-continued

| Compound Number | Structure | Physical Data MS (m/z) |
|---|---|---|
| 38 | 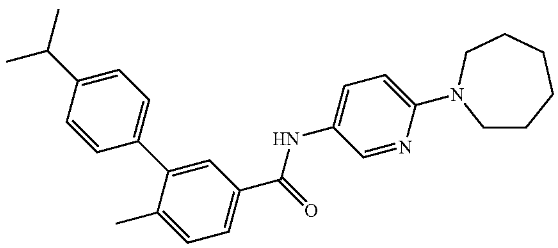 [SMILES: Cc1ccc(C(=O)Nc2ccc(N3CCCCCC3)nc2)cc1-c1ccc(C(C)C)cc1] | LC-MS m/z 428.2 (M + 1). |
| 39 | 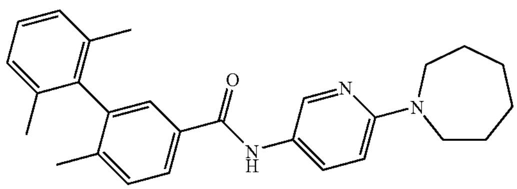 [SMILES: Cc1ccc(C(=O)Nc2ccc(N3CCCCCC3)nc2)cc1-c1c(C)cccc1C] | LC-MS m/z 414.2 (M + 1). |
| 40 | 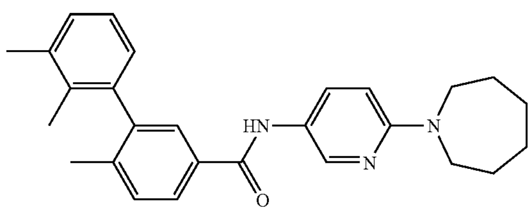 [SMILES: Cc1ccc(C(=O)Nc2ccc(N3CCCCCC3)nc2)cc1-c1cccc(C)c1C] | LC-MS m/z 414.2 (M + 1). |
| 41 | 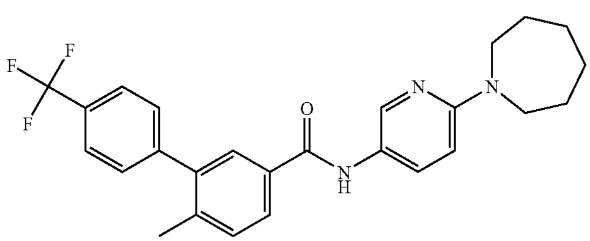 [SMILES: Cc1ccc(C(=O)Nc2ccc(N3CCCCCC3)nc2)cc1-c1ccc(C(F)(F)F)cc1] | LC-MS m/z 454.2 (M + 1). |
| 42 | 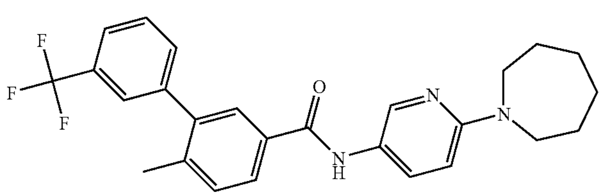 [SMILES: Cc1ccc(C(=O)Nc2ccc(N3CCCCCC3)nc2)cc1-c1cccc(C(F)(F)F)c1] | LC-MS m/z 454.2 (M + 1). |
| 43 | 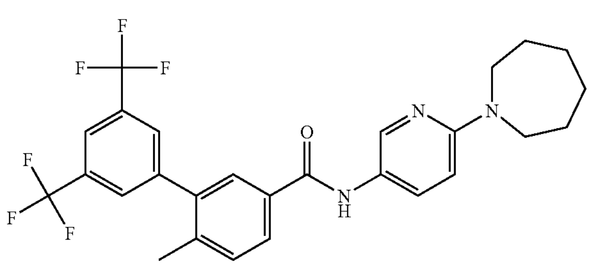 [SMILES: Cc1ccc(C(=O)Nc2ccc(N3CCCCCC3)nc2)cc1-c1cc(C(F)(F)F)cc(C(F)(F)F)c1] | LC-MS m/z 522.2 (M + 1). |

TABLE 1-continued

| Compound Number | Structure | Physical Data MS (m/z) |
|---|---|---|
| 44 | 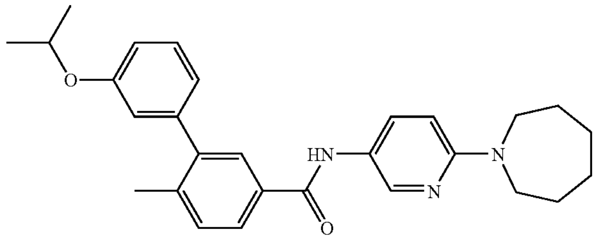 [SMILES: Cc1ccc(C(=O)Nc2ccc(N3CCCCCC3)nc2)cc1-c1cccc(OC(C)C)c1] | LC-MS m/z 444.2 (M + 1). |
| 45 | 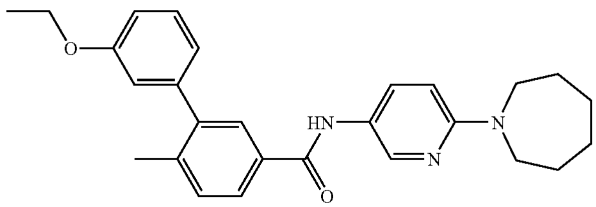 [SMILES: CCOc1cccc(-c2cc(C(=O)Nc3ccc(N4CCCCCC4)nc3)ccc2C)c1] | LC-MS m/z 430.2 (M + 1). |
| 46 | 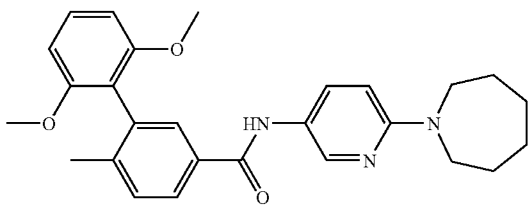 [SMILES: COc1cccc(OC)c1-c1cc(C(=O)Nc2ccc(N3CCCCCC3)nc2)ccc1C] | LC-MS m/z 446.2 (M + 1). |
| 47 | 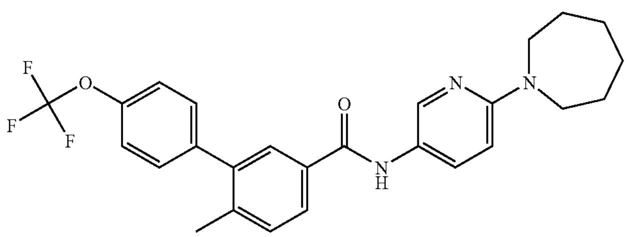 [SMILES: Cc1ccc(C(=O)Nc2ccc(N3CCCCCC3)nc2)cc1-c1ccc(OC(F)(F)F)cc1] | LC-MS m/z 470.2 (M + 1). |
| 48 | 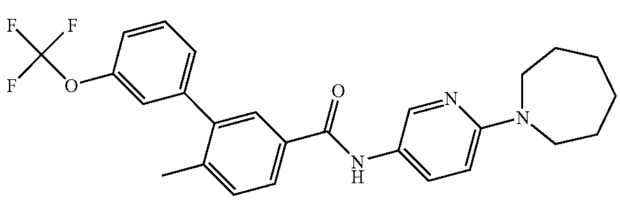 [SMILES: Cc1ccc(C(=O)Nc2ccc(N3CCCCCC3)nc2)cc1-c1cccc(OC(F)(F)F)c1] | LC-MS m/z 470.2 (M + 1). |
| 49 | 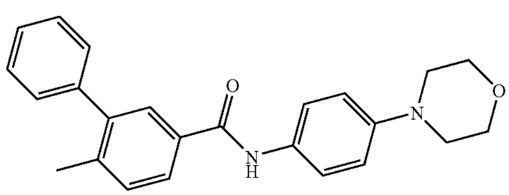 [SMILES: Cc1ccc(C(=O)Nc2ccc(N3CCOCC3)cc2)cc1-c1ccccc1] | LC-MS m/z 373.2 (M + 1). |
| 50 | 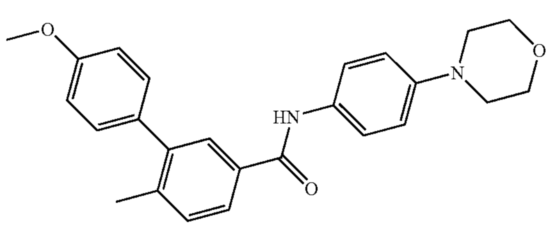 [SMILES: COc1ccc(-c2cc(C(=O)Nc3ccc(N4CCOCC4)cc3)ccc2C)cc1] | LC-MS m/z 403.2 (M + 1). |

TABLE 1-continued
| Compound Number | Structure | Physical Data MS (m/z) |
|---|---|---|
| 51 | 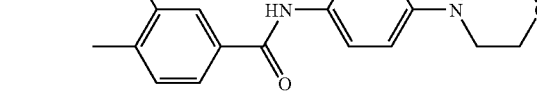 | LC-MS m/z 403.2 (M + 1). |
| 52 | 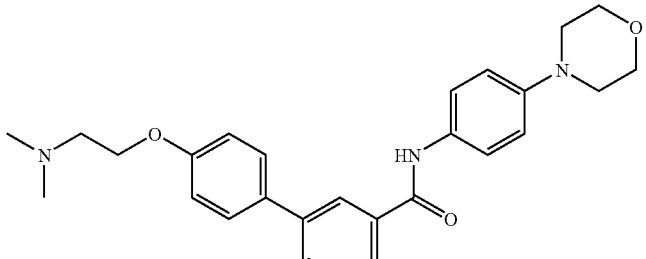 | LC-MS m/z 460.2 (M + 1). |
| 53 | 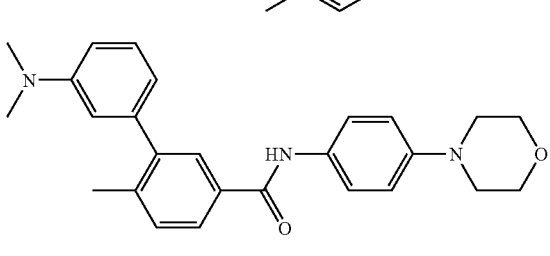 | LC-MS m/z 416.2 (M + 1). |
| 54 | 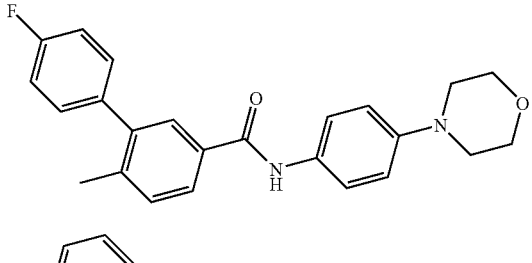 | LC-MS m/z 391.2 (M + 1). |
| 55 | 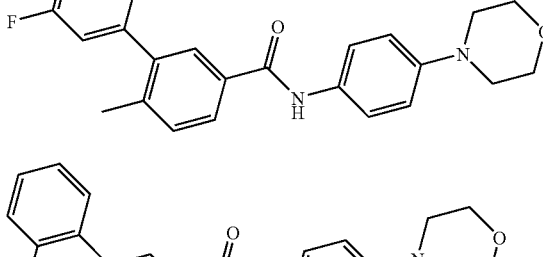 | LC-MS m/z 391.2 (M + 1). |
| 56 | 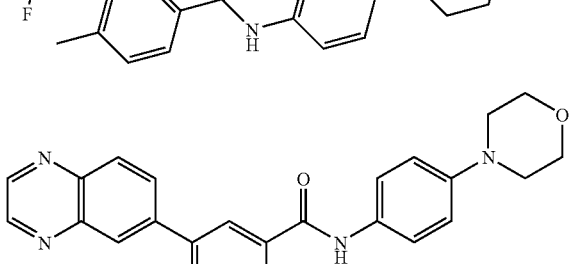 | LC-MS m/z 391.2 (M + 1). |
| 57 | 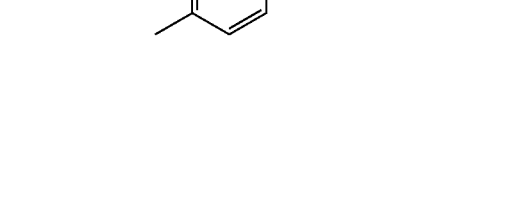 | LC-MS m/z 425.2 (M + 1). |

TABLE 1-continued

| Compound Number | Structure | Physical Data MS (m/z) |
|---|---|---|
| 58 | 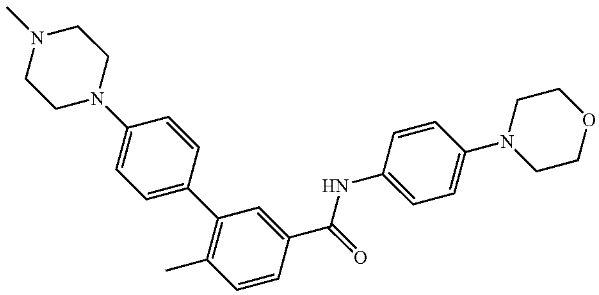 [SMILES: Cc1ccc(C(=O)Nc2ccc(N3CCOCC3)cc2)cc1-c1ccc(N2CCN(C)CC2)cc1] | LC-MS m/z 471.2 (M + 1). |
| 59 | 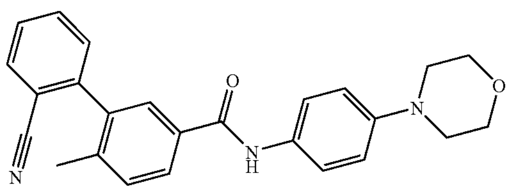 [SMILES: Cc1ccc(C(=O)Nc2ccc(N3CCOCC3)cc2)cc1-c1ccccc1C#N] | LC-MS m/z 398.2 (M + 1). |
| 60 | 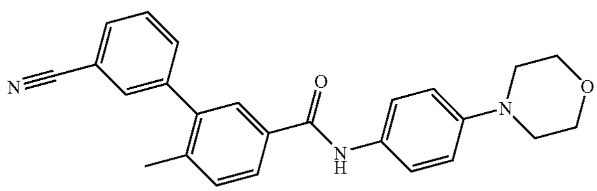 [SMILES: Cc1ccc(C(=O)Nc2ccc(N3CCOCC3)cc2)cc1-c1cccc(C#N)c1] | LC-MS m/z 398.2 (M + 1). |
| 61 | 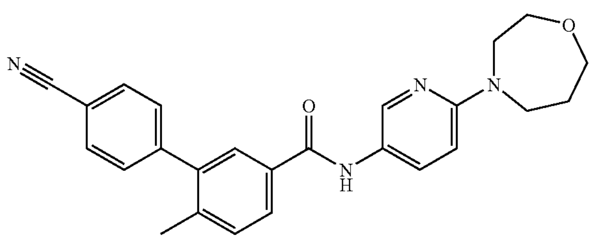 [SMILES: Cc1ccc(C(=O)Nc2ccc(N3CCCOCC3)nc2)cc1-c1ccc(C#N)cc1] | LC-MS m/z 413.2 (M + 1). |
| 62 | 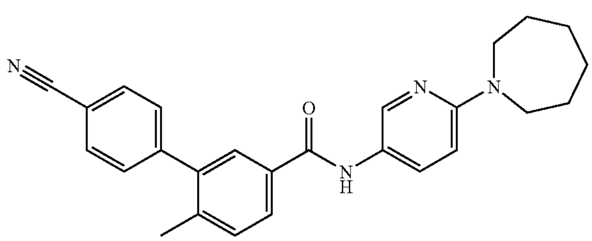 [SMILES: Cc1ccc(C(=O)Nc2ccc(N3CCCCCC3)nc2)cc1-c1ccc(C#N)cc1] | LC-MS m/z 411.2 (M + 1). |
| 63 | 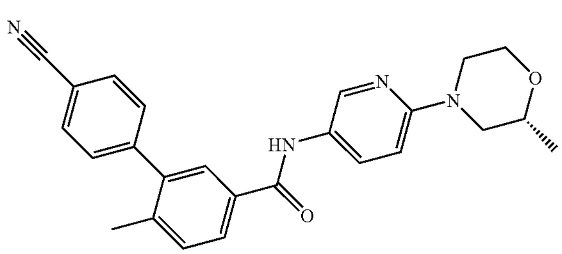 [SMILES: Cc1ccc(C(=O)Nc2ccc(N3CCO[C@H](C)C3)nc2)cc1-c1ccc(C#N)cc1] | LC-MS m/z 413.2 (M + 1). |

TABLE 1-continued
| Compound Number | Structure | Physical Data MS (m/z) |
|---|---|---|
| 64 | 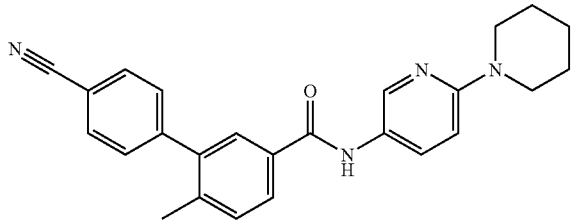 [SMILES: Cc1ccc(C(=O)Nc2ccc(N3CCCCC3)nc2)cc1-c1ccc(C#N)cc1] | LC-MS m/z 397.2 (M + 1). |
| 65 | 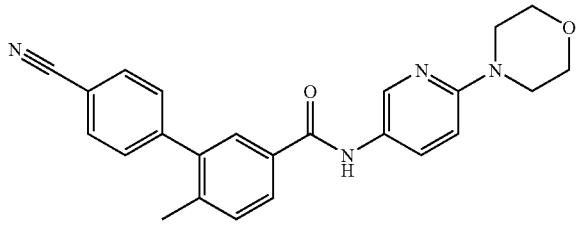 [SMILES: Cc1ccc(C(=O)Nc2ccc(N3CCOCC3)nc2)cc1-c1ccc(C#N)cc1] | LC-MS m/z 399.2 (M + 1). |
| 66 | 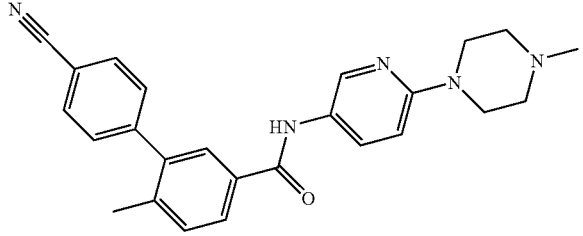 [SMILES: Cc1ccc(C(=O)Nc2ccc(N3CCN(C)CC3)nc2)cc1-c1ccc(C#N)cc1] | LC-MS m/z 412.2 (M + 1). |
| 67 | 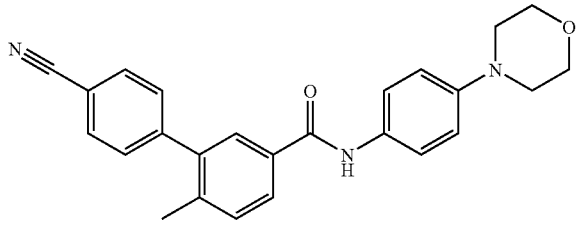 [SMILES: Cc1ccc(C(=O)Nc2ccc(N3CCOCC3)cc2)cc1-c1ccc(C#N)cc1] | LC-MS m/z 398.2 (M + 1). |
| 68 | 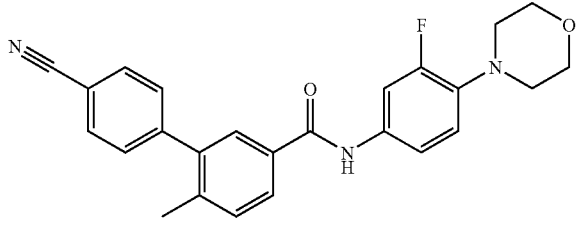 | LC-MS m/z 416.2 (M + 1). |
| 69 | 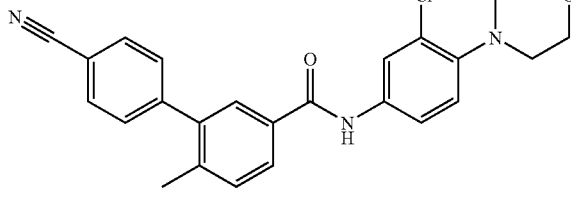 | LC-MS m/z 432.1 (M + 1). |

TABLE 1-continued

| Compound Number | Structure | Physical Data MS (m/z) |
|---|---|---|
| 70 | 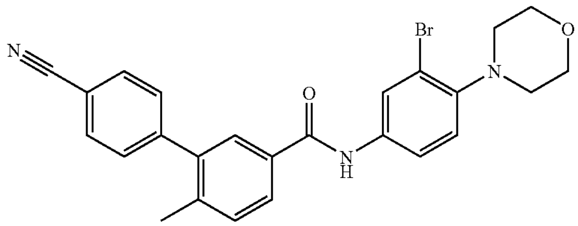 | LC-MS m/z 476.1 (M + 1). |
| 71 | 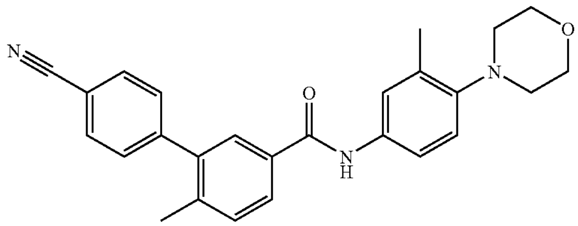 [SMILES: Cc1ccc(C(=O)Nc2ccc(N3CCOCC3)c(C)c2)cc1-c1ccc(C#N)cc1] | LC-MS m/z 412.2 (M + 1). |
| 72 | 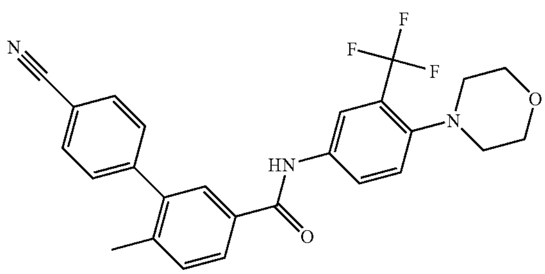 [SMILES: Cc1ccc(C(=O)Nc2ccc(N3CCOCC3)c(C(F)(F)F)c2)cc1-c1ccc(C#N)cc1] | LC-MS m/z 466.2 (M + 1). |
| 73 | 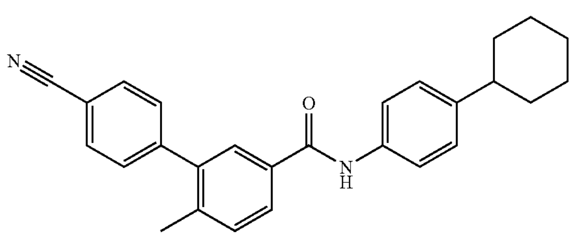 | LC-MS m/z 385.2 (M + 1). |
| 74 | 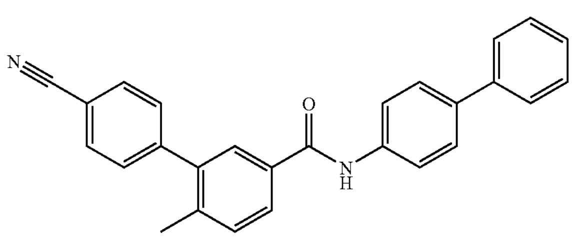 [SMILES: Cc1ccc(C(=O)Nc2ccc(-c3ccccc3)cc2)cc1-c1ccc(C#N)cc1] | LC-MS m/z 389.1 (M + 1). |
| 75 | 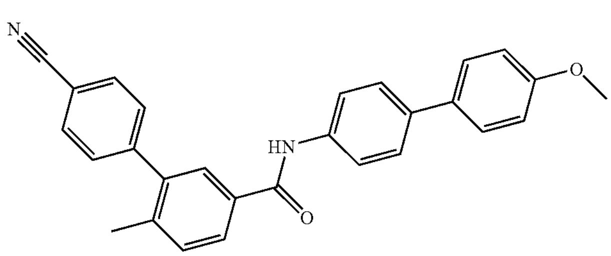 [SMILES: COc1ccc(-c2ccc(NC(=O)c3ccc(C)c(-c4ccc(C#N)cc4)c3)cc2)cc1] | LC-MS m/z 419.2 (M + 1). |

TABLE 1-continued

| Compound Number | Structure | Physical Data MS (m/z) |
|---|---|---|
| 76 | 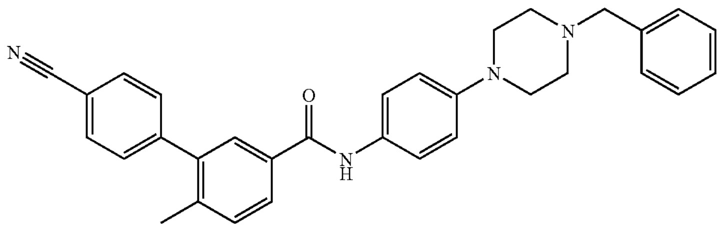 [SMILES: Cc1ccc(C(=O)Nc2ccc(N3CCN(Cc4ccccc4)CC3)cc2)cc1-c1ccc(C#N)cc1] | LC-MS m/z 487.2 (M + 1). |
| 77 | 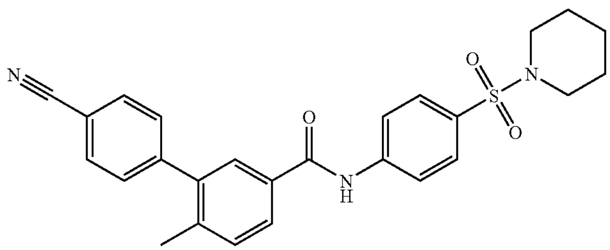 [SMILES: Cc1ccc(C(=O)Nc2ccc(S(=O)(=O)N3CCCCC3)cc2)cc1-c1ccc(C#N)cc1] | LC-MS m/z 460.2 (M + 1). |
| 78 | 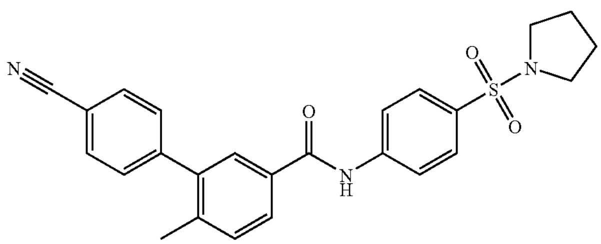 [SMILES: Cc1ccc(C(=O)Nc2ccc(S(=O)(=O)N3CCCC3)cc2)cc1-c1ccc(C#N)cc1] | LC-MS m/z 446.1 (M + 1). |
| 79 | 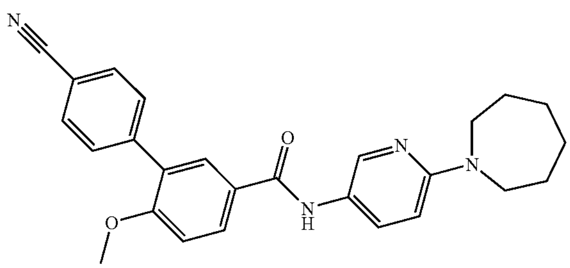 [SMILES: COc1ccc(C(=O)Nc2ccc(N3CCCCCC3)nc2)cc1-c1ccc(C#N)cc1] | LC-MS m/z 427.2 (M + 1). |
| 80 | 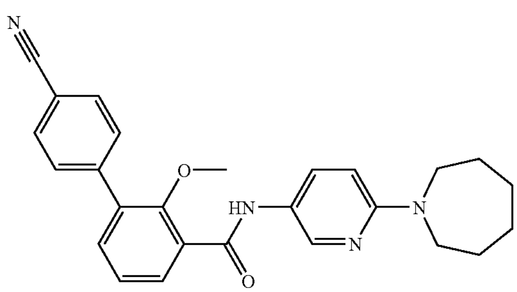 [SMILES: COc1c(C(=O)Nc2ccc(N3CCCCCC3)nc2)cccc1-c1ccc(C#N)cc1] | LC-MS m/z 427.2 (M + 1) |
| 81 | 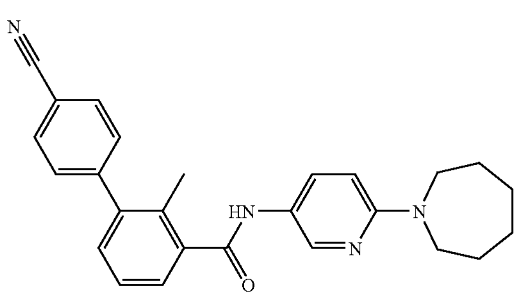 [SMILES: Cc1c(C(=O)Nc2ccc(N3CCCCCC3)nc2)cccc1-c1ccc(C#N)cc1] | LC-MS m/z 411.2 (M + 1) |

TABLE 1-continued
| Compound Number | Structure | Physical Data MS (m/z) |
|---|---|---|
| 82 | 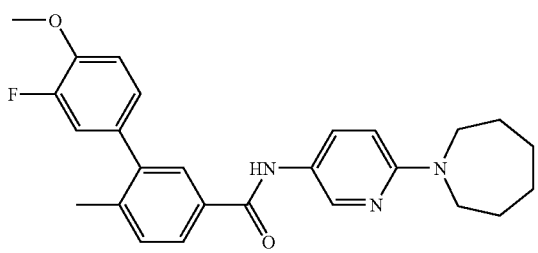 [SMILES: COc1ccc(-c2cc(C(=O)Nc3ccc(N4CCCCCC4)nc3)ccc2C)cc1F] | LC-MS m/z 434.2 (M + 1) |
| 83 | 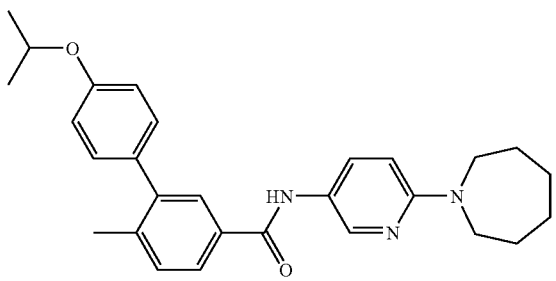 [SMILES: Cc1ccc(C(=O)Nc2ccc(N3CCCCCC3)nc2)cc1-c1ccc(OC(C)C)cc1] | LC-MS m/z 444.3 (M + 1) |
| 84 | 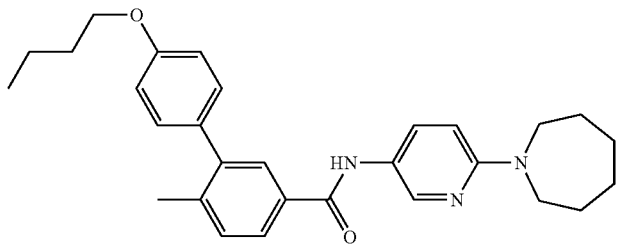 [SMILES: CCCCOc1ccc(-c2cc(C(=O)Nc3ccc(N4CCCCCC4)nc3)ccc2C)cc1] | LC-MS m/z 458.3 (M + 1) |
| 85 | 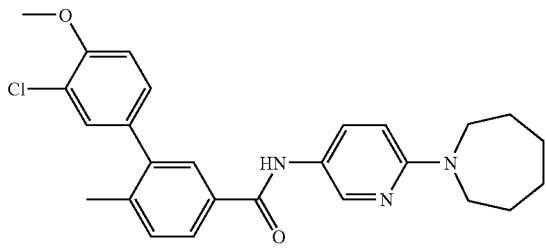 [SMILES: COc1ccc(-c2cc(C(=O)Nc3ccc(N4CCCCCC4)nc3)ccc2C)cc1Cl] | LC-MS m/z 450.2 (M + 1) |
| 86 | 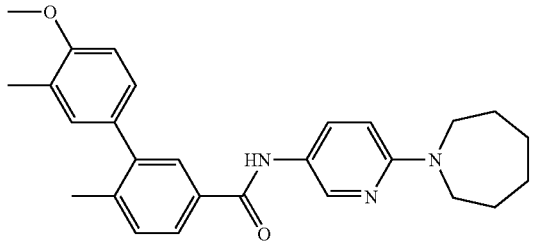 | LC-MS m/z 430.2 (M + 1) |

TABLE 1-continued

| Compound Number | Structure | Physical Data MS (m/z) |
|---|---|---|
| 87 | 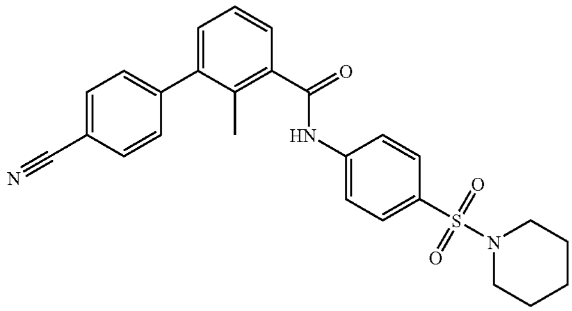 [SMILES: Cc1c(C(=O)Nc2ccc(S(=O)(=O)N3CCCCC3)cc2)cccc1-c1ccc(C#N)cc1] | LC-MS m/z 460.2 (M + 1) |
| 88 | 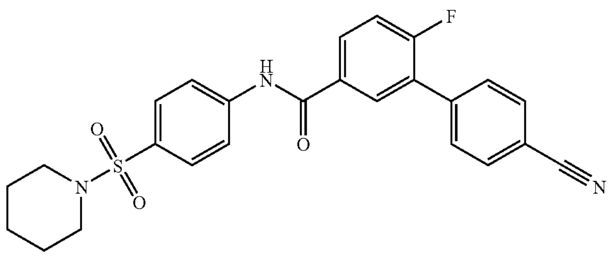 [SMILES: N#Cc1ccc(-c2cc(C(=O)Nc3ccc(S(=O)(=O)N4CCCCC4)cc3)ccc2F)cc1] | LC-MS m/z 464.1 (M + 1) |
| 89 | 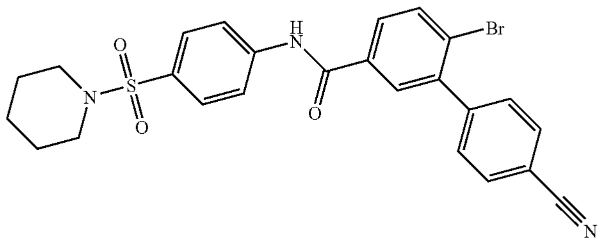 [SMILES: N#Cc1ccc(-c2cc(C(=O)Nc3ccc(S(=O)(=O)N4CCCCC4)cc3)ccc2Br)cc1] | LC-MS m/z 524.1 (M + 1) |
| 90 | 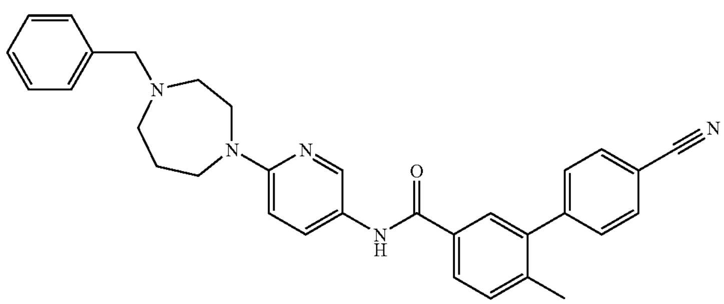 [SMILES: Cc1ccc(C(=O)Nc2ccc(N3CCCN(Cc4ccccc4)CC3)nc2)cc1-c1ccc(C#N)cc1] | LC-MS m/z 502.3 (M + 1) |
| 91 | 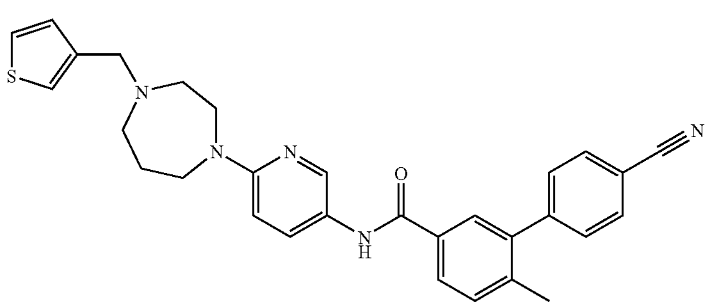 [SMILES: Cc1ccc(C(=O)Nc2ccc(N3CCCN(Cc4ccsc4)CC3)nc2)cc1-c1ccc(C#N)cc1] | LC-MS m/z 508.2 (M + 1) |

TABLE 1-continued

| Compound Number | Structure | Physical Data MS (m/z) |
|---|---|---|
| 92 | 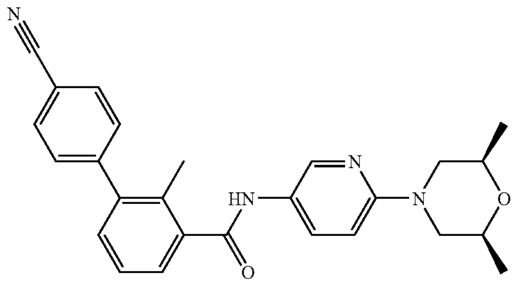 [SMILES: Cc1c(C(=O)Nc2ccc(N3C[C@@H](C)O[C@@H](C)C3)nc2)cccc1-c1ccc(C#N)cc1] | LC-MS m/z 427.2 (M + 1) |
| 93 | 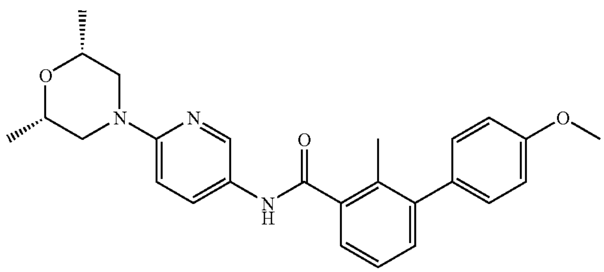 | LC-MS m/z 432.2 (M + 1) |
| 94 | 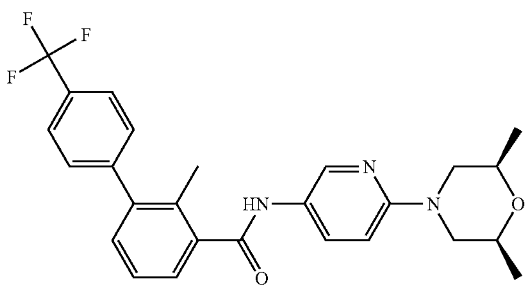 [SMILES: Cc1c(C(=O)Nc2ccc(N3C[C@@H](C)O[C@@H](C)C3)nc2)cccc1-c1ccc(C(F)(F)F)cc1] | LC-MS m/z 470.2 (M + 1) |
| 95 | 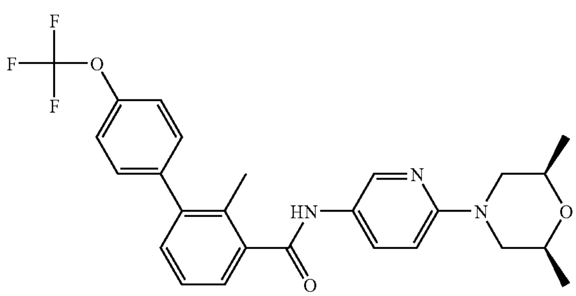 | LC-MS m/z 486.2 (M + 1) |
| 96 | 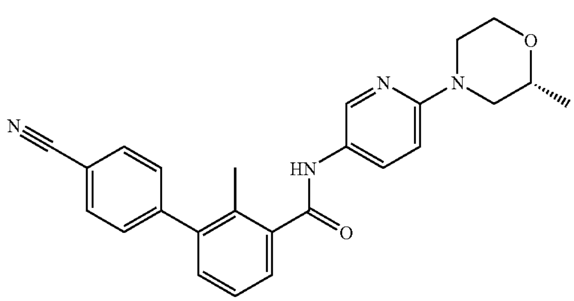 [SMILES: Cc1c(C(=O)Nc2ccc(N3CCO[C@H](C)C3)nc2)cccc1-c1ccc(C#N)cc1] | LC-MS m/z 413.2 (M + 1) |

TABLE 1-continued

| Compound Number | Structure | Physical Data MS (m/z) |
|---|---|---|
| 97 | 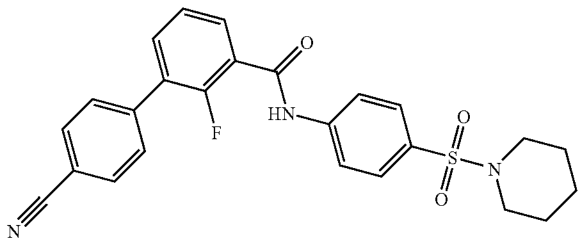 [SMILES: N#Cc1ccc(-c2cccc(C(=O)Nc3ccc(S(=O)(=O)N4CCCCC4)cc3)c2F)cc1] | LC-MS m/z 464.1 (M + 1) |
| 98 | 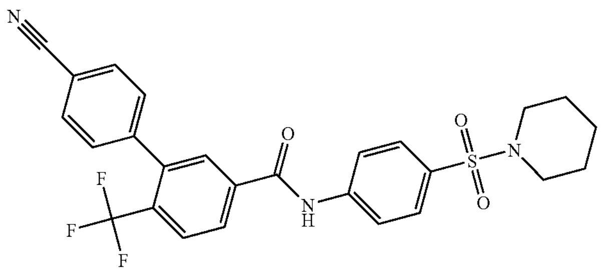 [SMILES: N#Cc1ccc(-c2cc(C(=O)Nc3ccc(S(=O)(=O)N4CCCCC4)cc3)ccc2C(F)(F)F)cc1] | LC-MS m/z 514.1 (M + 1) |
| 99 | 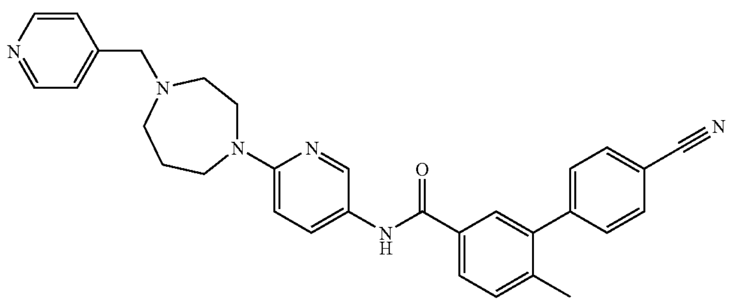 [SMILES: Cc1ccc(C(=O)Nc2ccc(N3CCCN(Cc4ccncc4)CC3)nc2)cc1-c1ccc(C#N)cc1] | LC-MS m/z 503.3 (M + 1) |
| 100 | 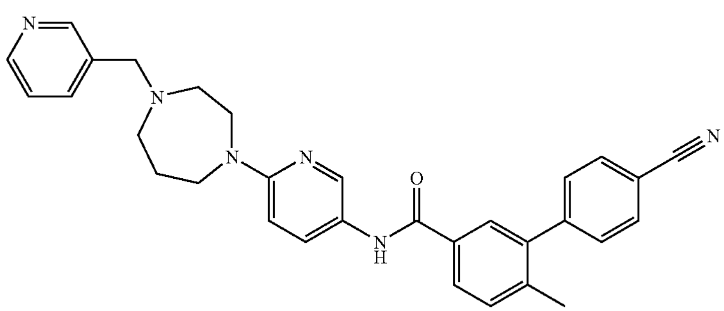 | LC-MS m/z 503.3 (M + 1) |
| 101 | 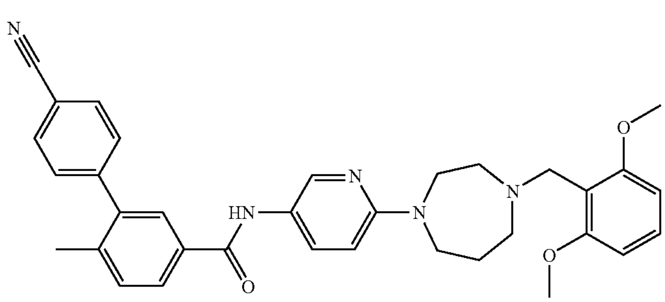 [SMILES: COc1cccc(OC)c1CN1CCCN(c2ccc(NC(=O)c3ccc(C)c(-c4ccc(C#N)cc4)c3)cn2)CC1] | LC-MS m/z 562.3 (M + 1) |

TABLE 1-continued

| Compound Number | Structure | Physical Data MS (m/z) |
|---|---|---|
| 102 | 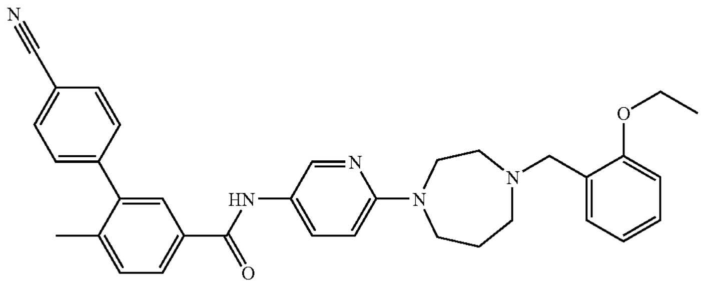 [SMILES: CCOc1ccccc1CN1CCCN(c2ccc(NC(=O)c3ccc(C)c(-c4ccc(C#N)cc4)c3)cn2)CC1] | LC-MS m/z 546.3 (M + 1) |
| 103 | 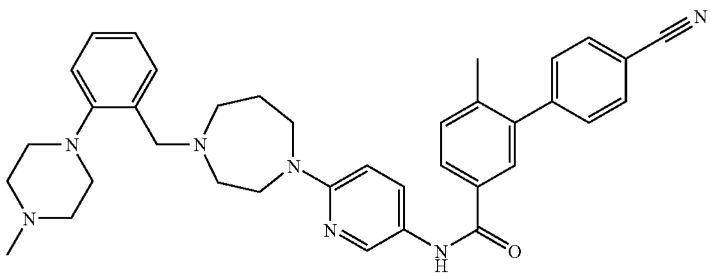 [SMILES: Cc1ccc(C(=O)Nc2ccc(N3CCCN(Cc4ccccc4N4CCN(C)CC4)CC3)nc2)cc1-c1ccc(C#N)cc1] | LC-MS m/z 600.3 (M + 1) |
| 104 | 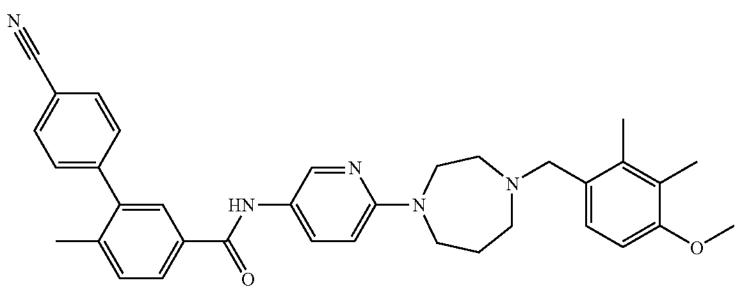 [SMILES: COc1ccc(CN2CCCN(c3ccc(NC(=O)c4ccc(C)c(-c5ccc(C#N)cc5)c4)cn3)CC2)c(C)c1C] | LC-MS m/z 560.3 (M + 1) |
| 105 | 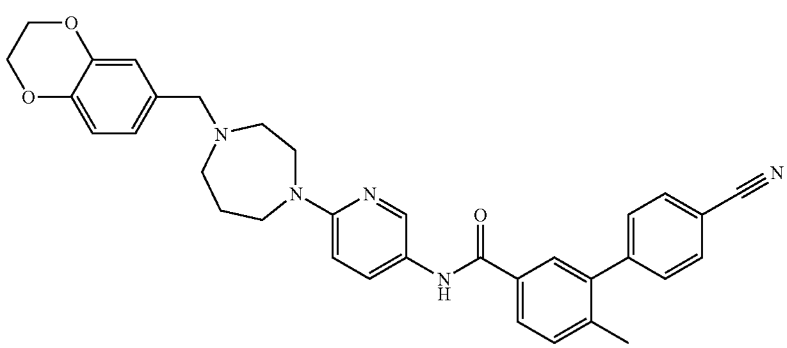 [SMILES: Cc1ccc(C(=O)Nc2ccc(N3CCCN(Cc4ccc5c(c4)OCCO5)CC3)nc2)cc1-c1ccc(C#N)cc1] | LC-MS m/z 560.3 (M + 1) |
| 106 | 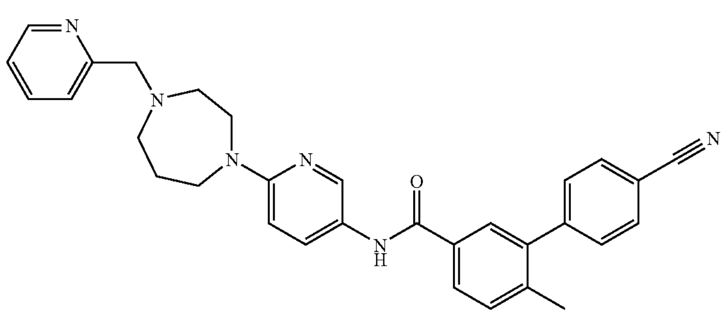 [SMILES: Cc1ccc(C(=O)Nc2ccc(N3CCCN(Cc4ccccn4)CC3)nc2)cc1-c1ccc(C#N)cc1] | LC-MS m/z 503.3 (M + 1) |

TABLE 1-continued
| Compound Number | Structure | Physical Data MS (m/z) |
|---|---|---|
| 107 | 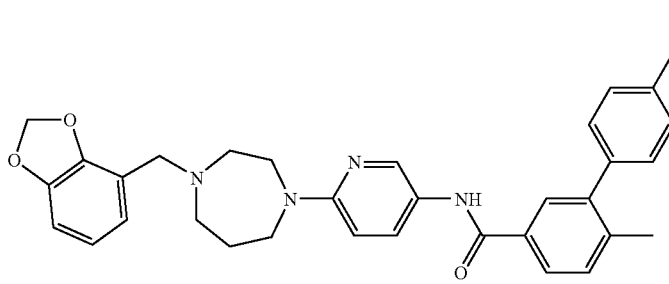 | LC-MS m/z 546.2 (M + 1) |
| 108 | 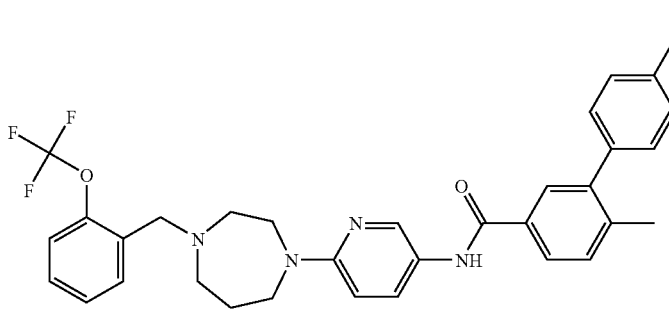 | LC-MS m/z 586.2 (M + 1) |
| 109 | 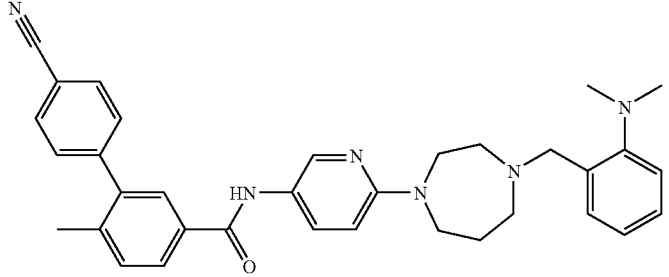 [SMILES: Cc1ccc(C(=O)Nc2ccc(N3CCCN(Cc4ccccc4N(C)C)CC3)nc2)cc1-c1ccc(C#N)cc1] | LC-MS m/z 545.3 (M + 1) |
| 110 | 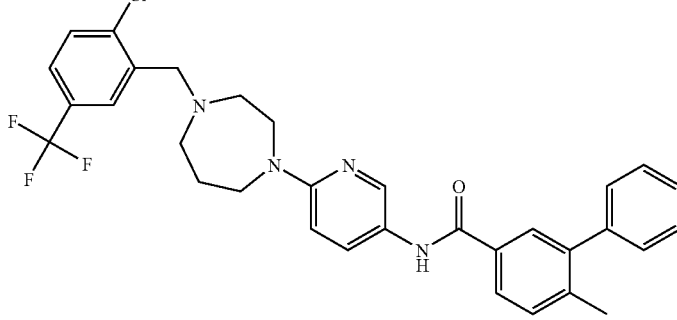 | LC-MS m/z 604.2 (M + 1) |
| 111 | 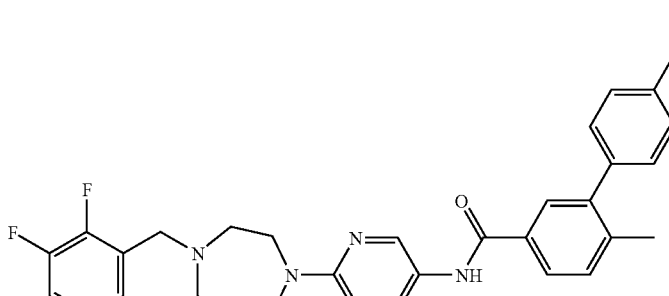 | LC-MS m/z 538.2 (M + 1) |

TABLE 1-continued

| Compound Number | Structure | Physical Data MS (m/z) |
|---|---|---|
| 112 | 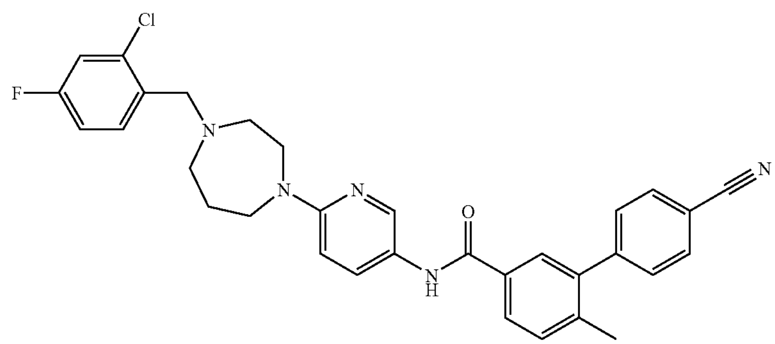 [SMILES: Cc1ccc(C(=O)Nc2ccc(N3CCCN(Cc4ccc(F)cc4Cl)CC3)nc2)cc1-c1ccc(C#N)cc1] | LC-MS m/z 554.2 (M + 1) |
| 113 | 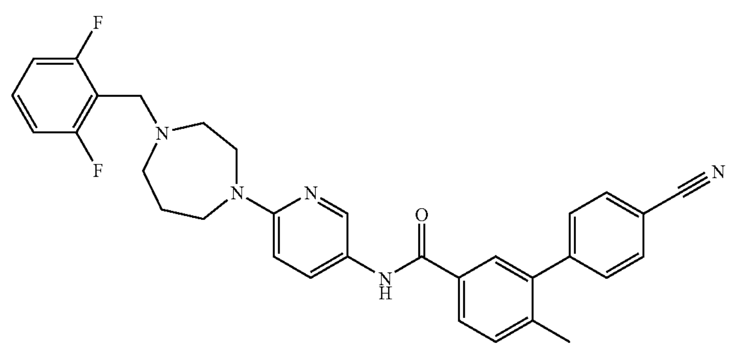 [SMILES: Cc1ccc(C(=O)Nc2ccc(N3CCCN(Cc4c(F)cccc4F)CC3)nc2)cc1-c1ccc(C#N)cc1] | LC-MS m/z 538.2 (M + 1) |
| 114 | 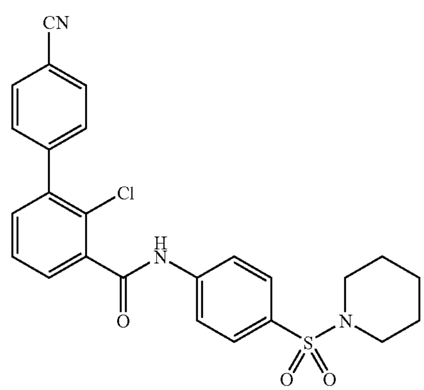 [SMILES: N#Cc1ccc(-c2cccc(C(=O)Nc3ccc(S(=O)(=O)N4CCCCC4)cc3)c2Cl)cc1] | LC-MS m/z 480.1 (M + 1) |
| 115 | 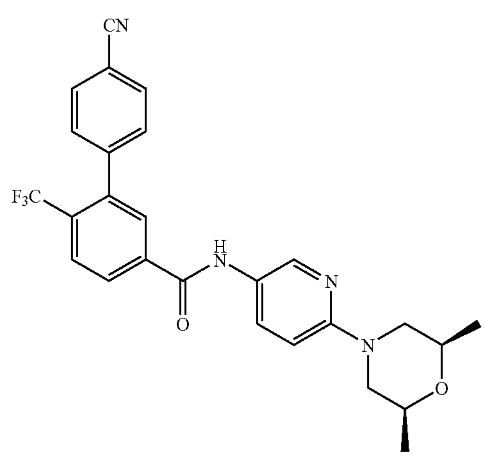 [SMILES: C[C@@H]1CN(c2ccc(NC(=O)c3ccc(C(F)(F)F)c(-c4ccc(C#N)cc4)c3)cn2)C[C@H](C)O1] | LC-MS m/z 481.2 (M + 1) |

TABLE 1-continued

| Compound Number | Structure | Physical Data MS (m/z) |
|---|---|---|
| 116 | 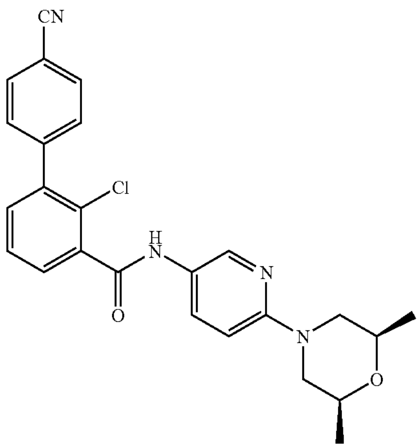 [SMILES: C[C@@H]1CN(c2ccc(NC(=O)c3cccc(-c4ccc(C#N)cc4)c3Cl)cn2)C[C@H](C)O1] | LC-MS m/z 447.2 (M + 1) |
| 117 | 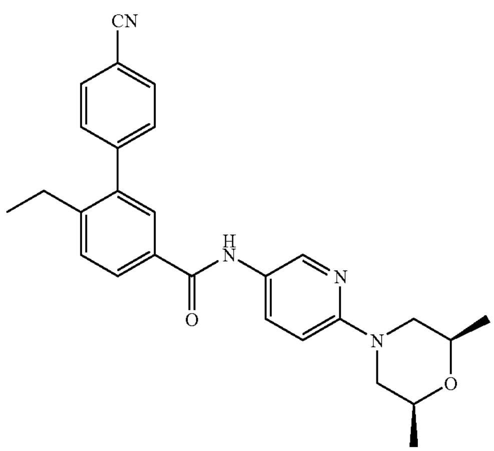 [SMILES: CCc1ccc(C(=O)Nc2ccc(N3C[C@@H](C)O[C@@H](C)C3)nc2)cc1-c1ccc(C#N)cc1] | LC-MS m/z 441.2 (M + 1) |
| 118 | 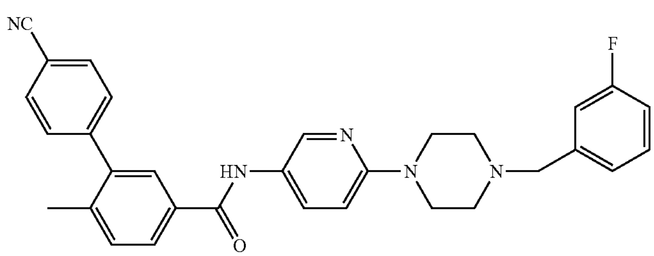 | LC-MS m/z 506.2 (M + 1) |
| 119 | 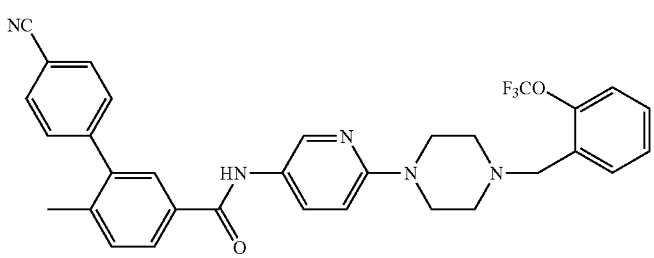 | LC-MS m/z 572.2 (M + 1) |

TABLE 1-continued

| Compound Number | Structure | Physical Data MS (m/z) |
|---|---|---|
| 120 | 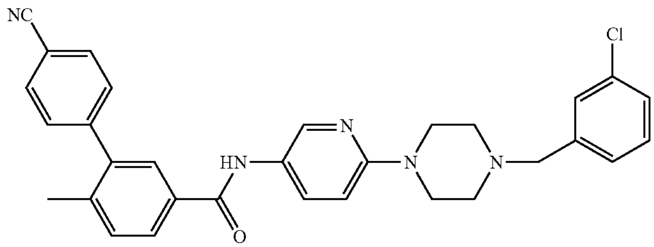 | LC-MS m/z 522.2 (M + 1) |
| 121 | 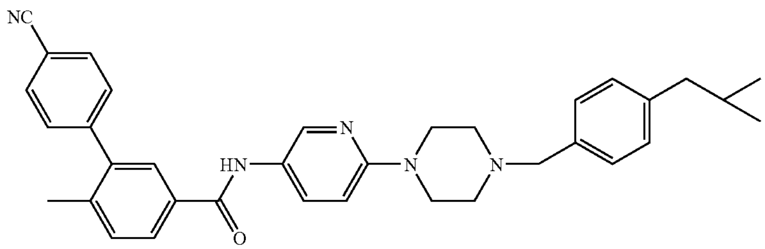 | LC-MS m/z 544.3 (M + 1) |
| 122 | 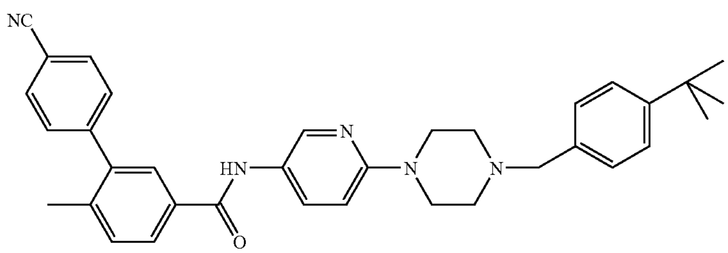 | LC-MS m/z 544.3 (M + 1) |
| 123 | 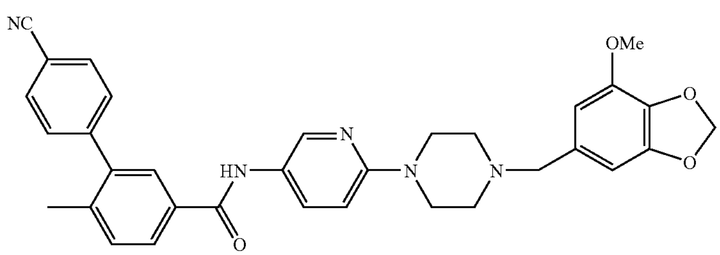 | LC-MS m/z 562.2 (M + 1) |
| 124 | 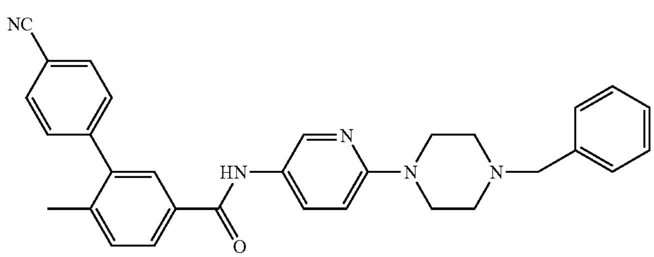 | LC-MS m/z 488.2 (M + 1) |
| 125 | 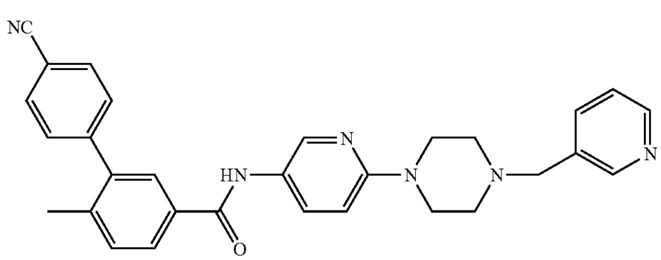 | LC-MS m/z 489.2 (M + 1) |

TABLE 1-continued

| Compound Number | Structure | Physical Data MS (m/z) |
|---|---|---|
| 126 | 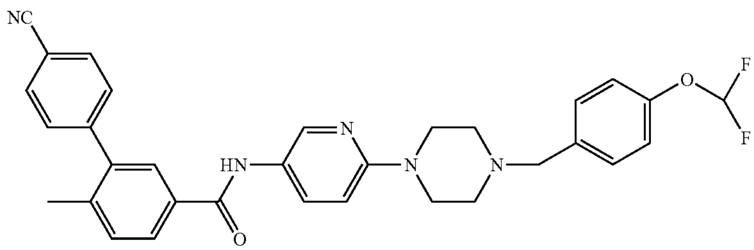 | LC-MS m/z 554.2 (M + 1) |
| 127 | 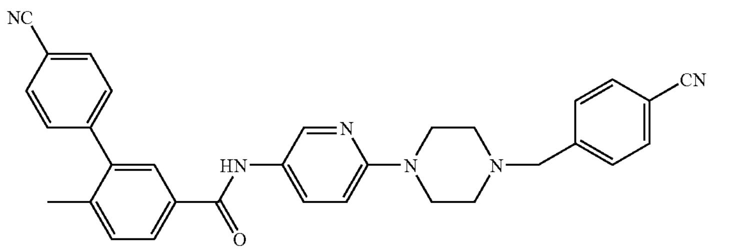 | LC-MS m/z 513.2 (M + 1) |
| 128 | 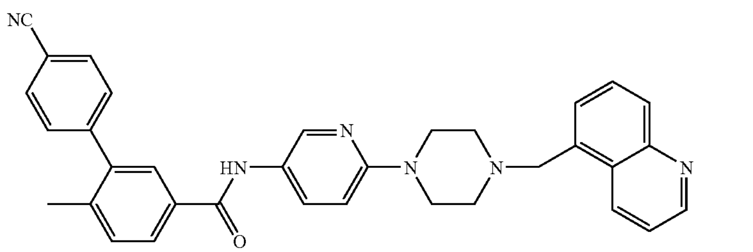 | LC-MS m/z 539.3 (M + 1) |
| 129 | 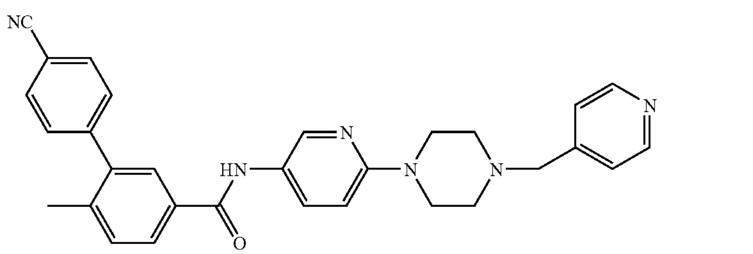 | LC-MS m/z 489.2 (M + 1) |
| 130 | 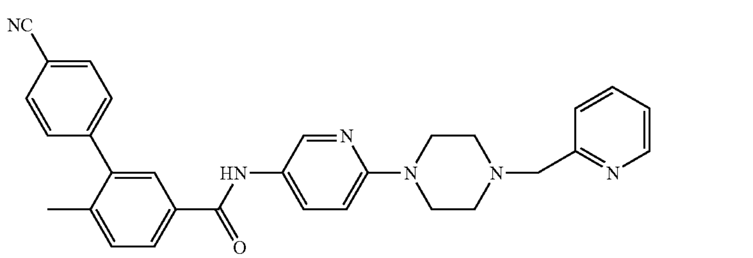 | LC-MS m/z 489.2 (M + 1) |
| 131 | 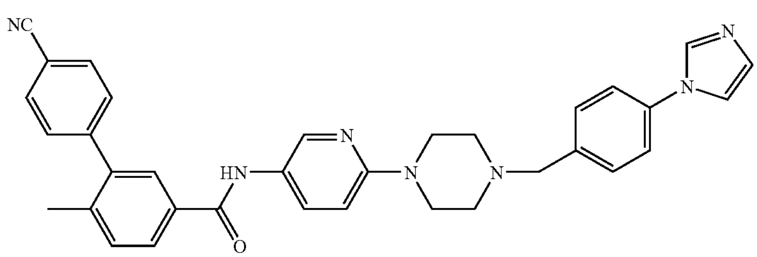 | LC-MS m/z 554.3 (M + 1) |

TABLE 1-continued

| Compound Number | Structure | Physical Data MS (m/z) |
|---|---|---|
| 132 | 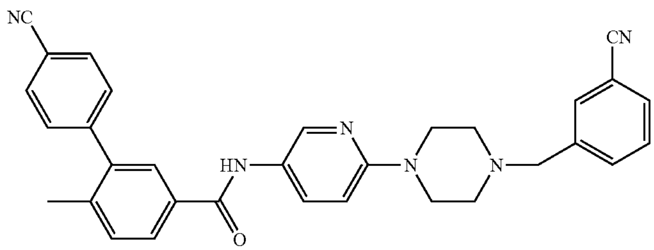 | LC-MS m/z 513.2 (M + 1) |
| 133 | 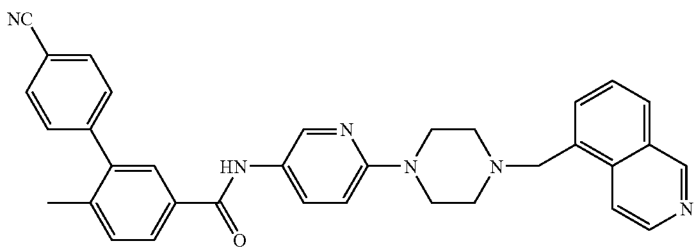 | LC-MS m/z 539.3 (M + 1) |
| 134 | 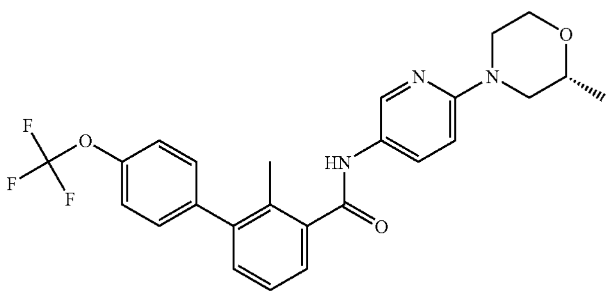 [SMILES: Cc1c(C(=O)Nc2ccc(N3CCO[C@H](C)C3)nc2)cccc1-c1ccc(OC(F)(F)F)cc1] | LC-MS m/z 472.1 (M + 1) |
| 135 | 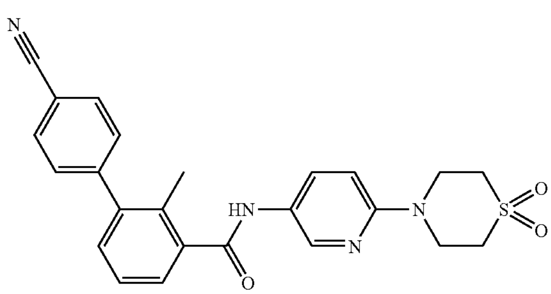 [SMILES: Cc1c(C(=O)Nc2ccc(N3CCS(=O)(=O)CC3)nc2)cccc1-c1ccc(C#N)cc1] | LC-MS m/z 447.1 (M + 1) |
| 136 | 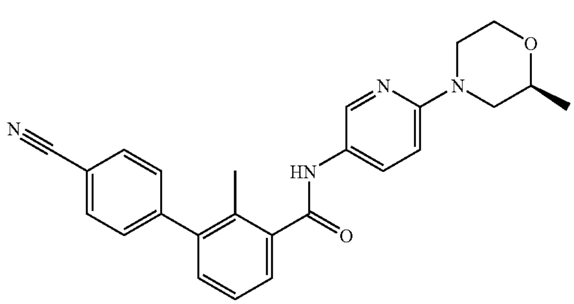 [SMILES: Cc1c(C(=O)Nc2ccc(N3CCO[C@@H](C)C3)nc2)cccc1-c1ccc(C#N)cc1] | LC-MS m/z 413.1 (M + 1) |

TABLE 1-continued

| Compound Number | Structure | Physical Data MS (m/z) |
|---|---|---|
| 137 | 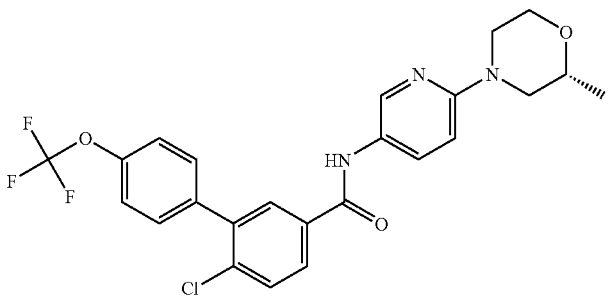 [SMILES: C[C@@H]1CN(c2ccc(NC(=O)c3ccc(Cl)c(-c4ccc(OC(F)(F)F)cc4)c3)cn2)CCO1] | LC-MS m/z 492.1 (M + 1) |
| 138 | 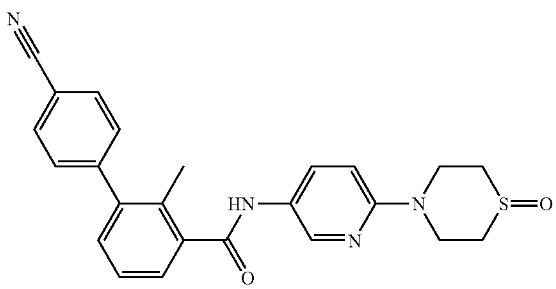 [SMILES: Cc1c(C(=O)Nc2ccc(N3CCS(=O)CC3)nc2)cccc1-c1ccc(C#N)cc1] | LC-MS m/z 431.1 (M + 1) |
| 139 | 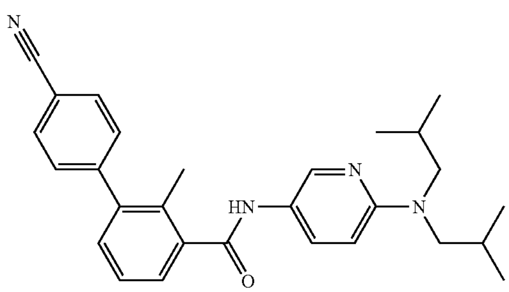 [SMILES: Cc1c(C(=O)Nc2ccc(N(CC(C)C)CC(C)C)nc2)cccc1-c1ccc(C#N)cc1] | LC-MS m/z 441.1 (M + 1) |
| 140 | 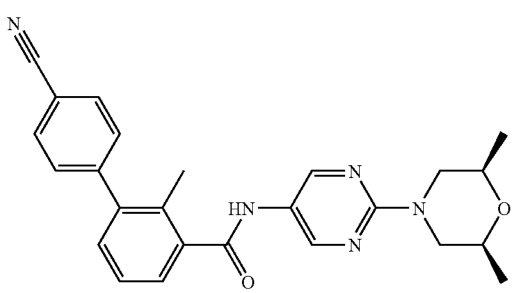 [SMILES: Cc1c(C(=O)Nc2cnc(N3C[C@@H](C)O[C@@H](C)C3)nc2)cccc1-c1ccc(C#N)cc1] | LC-MS m/z 428.2 (M + 1) |
| 141 | 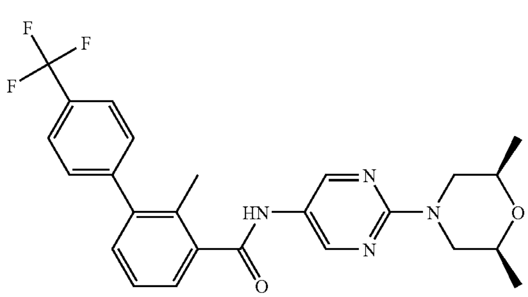 [SMILES: Cc1c(C(=O)Nc2cnc(N3C[C@@H](C)O[C@@H](C)C3)nc2)cccc1-c1ccc(C(F)(F)F)cc1] | LC-MS m/z 471.2 (M + 1) |

TABLE 1-continued

| Compound Number | Structure | Physical Data MS (m/z) |
|---|---|---|
| 142 | 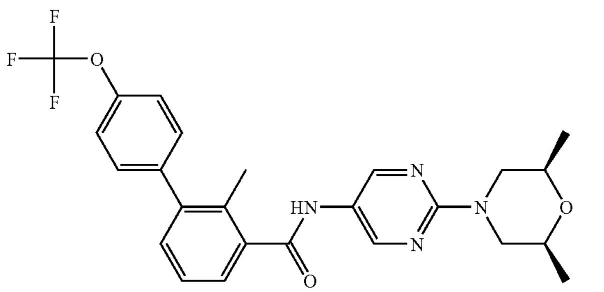 [SMILES: Cc1c(C(=O)Nc2cnc(N3C[C@@H](C)O[C@@H](C)C3)nc2)cccc1-c1ccc(OC(F)(F)F)cc1] | LC-MS m/z 487.2 (M + 1) |
| 143 | 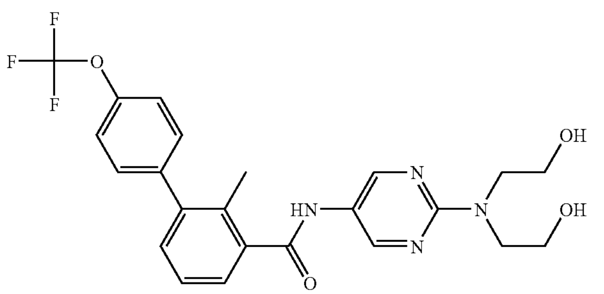 [SMILES: Cc1c(C(=O)Nc2cnc(N(CCO)CCO)nc2)cccc1-c1ccc(OC(F)(F)F)cc1] | LC-MS m/z 477.2 (M + 1) |
| 144 | 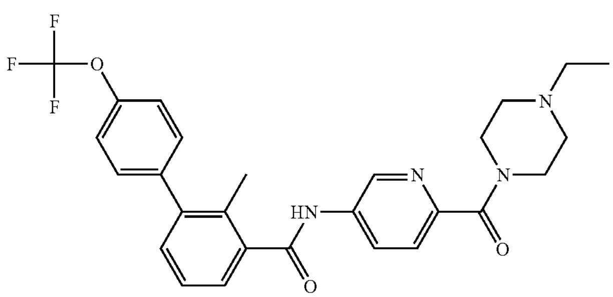 [SMILES: CCN1CCN(C(=O)c2ccc(NC(=O)c3cccc(-c4ccc(OC(F)(F)F)cc4)c3C)cn2)CC1] | LC-MS m/z 513.2 (M + 1) |
| 145 | 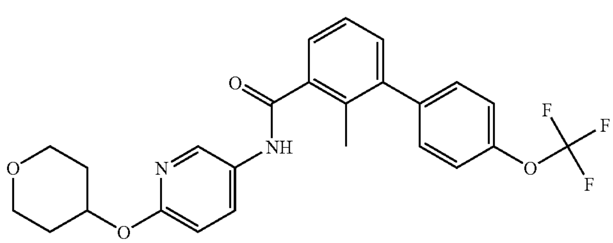 [SMILES: Cc1c(C(=O)Nc2ccc(OC3CCOCC3)nc2)cccc1-c1ccc(OC(F)(F)F)cc1] | LC-MS m/z 473.2 (M + 1) |
| 146 | 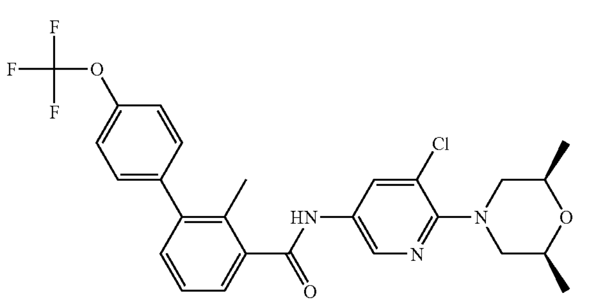 [SMILES: Cc1c(C(=O)Nc2cnc(N3C[C@@H](C)O[C@@H](C)C3)c(Cl)c2)cccc1-c1ccc(OC(F)(F)F)cc1] | LC-MS m/z 520.2 (M + 1) |

TABLE 1-continued

| Compound Number | Structure | Physical Data MS (m/z) |
|---|---|---|
| 147 | 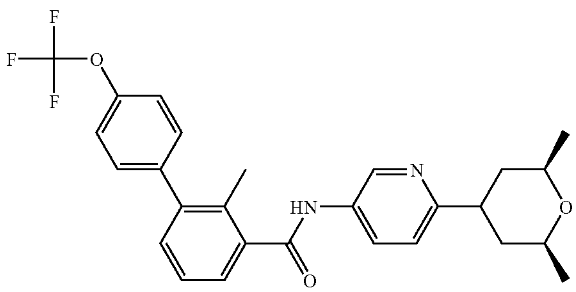 | LC-MS m/z 445.2 (M + 1) |
| 148 | 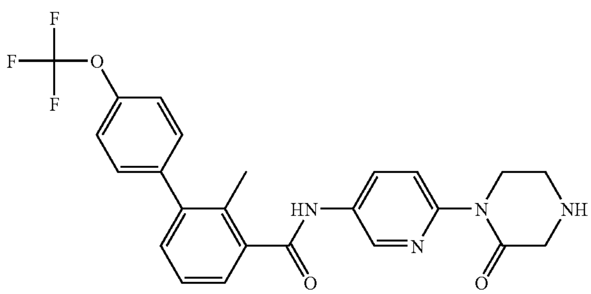 [SMILES: Cc1c(C(=O)Nc2ccc(N3CCNCC3=O)nc2)cccc1-c1ccc(OC(F)(F)F)cc1] | LC-MS m/z 471.2 (M + 1) |
| 149 | 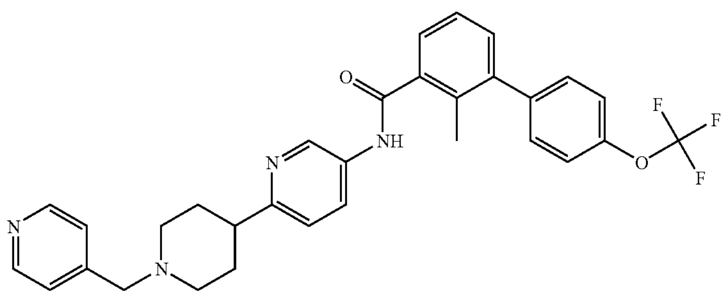 [SMILES: Cc1c(C(=O)Nc2ccc(C3CCN(Cc4ccncc4)CC3)nc2)cccc1-c1ccc(OC(F)(F)F)cc1] | LC-MS m/z 547.2 (M + 1) |
| 150 | 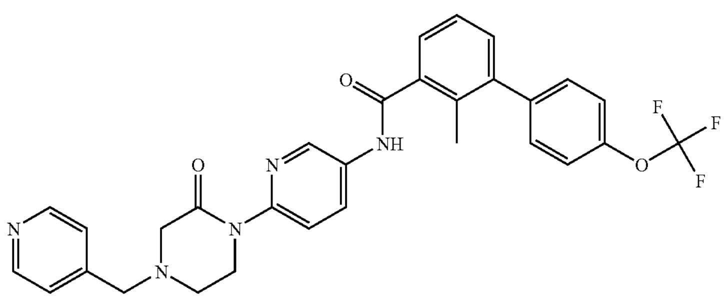 [SMILES: Cc1c(C(=O)Nc2ccc(N3CCN(Cc4ccncc4)CC3=O)nc2)cccc1-c1ccc(OC(F)(F)F)cc1] | LC-MS m/z 562.2 (M + 1) |
| 151 | 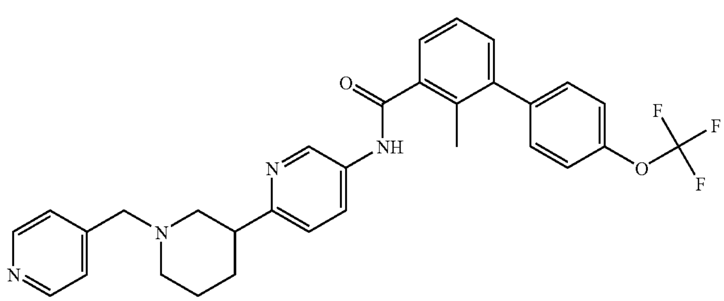 [SMILES: Cc1c(C(=O)Nc2ccc(C3CCCN(Cc4ccncc4)C3)nc2)cccc1-c1ccc(OC(F)(F)F)cc1] | LC-MS m/z 547.2 (M + 1) |

TABLE 1-continued

| Compound Number | Structure | Physical Data MS (m/z) |
|---|---|---|
| 152 | 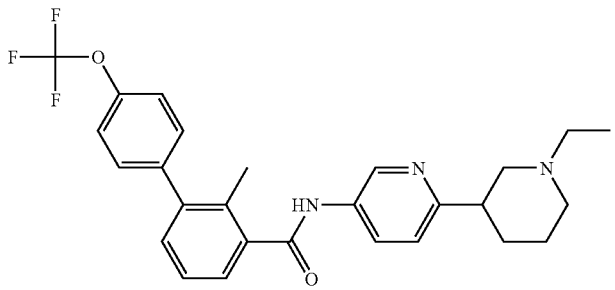 [SMILES: CCN1CCCC(c2ccc(NC(=O)c3cccc(-c4ccc(OC(F)(F)F)cc4)c3C)cn2)C1] | LC-MS m/z 484.2 (M + 1) |
| 153 | 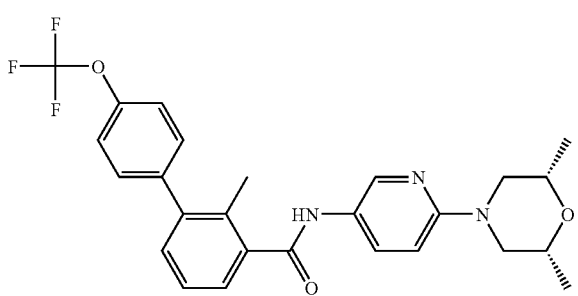 [SMILES: Cc1c(C(=O)Nc2ccc(N3C[C@@H](C)O[C@@H](C)C3)nc2)cccc1-c1ccc(OC(F)(F)F)cc1] | LC-MS m/z 486.2 (M + 1) |

General materials and methods for the analysis of compounds of the invention are described in PCT application number PCT/US2007/038171 "Compounds and Compositions for Treating Lymphoma and Myeloma"; Dierks and Warmuth. The full disclosure of this application is incorporated herein by reference in its entirety and for all purposes. Compounds of the present invention are assayed to evaluate their capacity to inhibit the hedgehog signaling pathway.

Gli-Luc Reporter Assay for Hh Pathway Inhibition

Mouse TM3 cells (obtained from American Type Culture Collection, ATCC, Manassas, Va.) are cultured in DMEM/F12 medium (Gibco/Invitrogen, Carlsbad, Calif.) supplemented with 5% heat inactivated horse serum and 2.5% FBS (Gibco/Invitrogen, Carlsbad, Calif.), 50 unit/mL penicillin and 50 μg/mL of streptomycin (Gibco/Invitrogen, Carlsbad, Calif.) at 37° C. with 5% $CO_2$ in air atmosphere. TM3 cells were transfected with pTA-8×Gli-Luc reporter plasmid. A stably transfected clone termed TMHh-12 was selected. TMHh-12 clone showed good response to Shh-N stimulation. To evaluate the IC50s of the antagonists, 8000 TMHh-12 cells were plated into each wells in 384-well plates with 50% DMEM/F12 medium supplemented with 2% FBS. After 12 hours, Hh pathway is activated by adding recombinant mouse Shh protein (expressed in E. coli, 8 μg/mL) or by adding Smo agonists. The testing compounds are added into plates with different concentrations. After 48 hours, the firefly luciferase luciferase activities are assayed with the Bright-Glo™ Luciferase Assay System (Promega, Madison, Wis.). The $IC_{50}$ is measured when the effect of the compound reduces the luminescence signal by 50%. Toxicity of these compounds are evaluated in TM3 cells using CellTiter Glo assays or by TM3-Luc cell line (a TM3 cell stably transfected with a constitutive luciferase expression vector).

Compounds of Formula I preferably have an $EC_{50}$ of less than 500 nM, more preferable less than 200 nM.

Inhibiting Hh Pathway Abrogates Lymphoma Expansion In Vivo

Stroma produced hedgehog ligands are important growth and survival factors for primary lymphoma cells under in-vitro culture conditions. Growth and expansion of lymphoma cells in-vivo is also dependent on Hh signalling. 1e6 lymphoma cells expressing luciferase were injected into syngeneic C57BL/6 mice. On day 2 post-injection, the mice were treated with either vehicle control or a compound of the invention (50, 25, 10 and 5 mg/kg/bid) for 10 days by oral administration. Luciferase levels were measured by bioluminescence imaging 3 times per week. Ten days post-injection, the control group shows high luminescence in the lymph nodes and spleens of all injected mice. Mice treated with a compound of the invention at 50, 25 and 10 mg/kg/bid showed a reduction of the luminescence signal to less than 10% compared to the control group (T/C below 10%). 5 mg/kg bid dosing group showed a partial response with a T/C from 40%. Therefore we conclude that hedgehog pathway inhibition reduces lymphoma growth in mice.

For example, compound 153 of table 1, reaches full efficacy, that is the presence of compound 153 completely blocks lymphoma cell expansion, at 50 mg/kg/day.

Embryonic Skin Punch Assay

Compounds of the invention are tested from their ability to treat non-melanoma skin cancer, i.e. basal cell carcinoma lesions using the skin punch assay. Mouse embryos from Ptch$^{+/-}$-LacZ mice, are collected and killed at late gestation (embryonic day 17.5) and their skins excised. Circular punches (4 mm in diameter are placed in a collagen-coated Transwell (BIOCOAT cell Culture Insert, Becton Dickinson Labware, Bedford, Mass.) and cultured at the air-liquid interface, with the epidermis side facing up. The culture medium contains 5% FBS in DMEM/F12 (3:1) with added epidermal growth factor, insulin, and hydrocortisone. To induce formation of basaloid nests, punches are grown in the presence of 1-2 μg/ml Shh for 4 or more days. Effects of compounds of the invention are tested by adding at the time of Shh addition or after 6 days of Shh pretreatment. Compounds of the invention show full inhibition (preventing lesion formation) at concentrations of 1 μM or less.

Compounds of Formula I preferably have an EC$_{50}$ of less than 500 nM, more preferable less than 200 nM to block basanoid formation. For example, compound 153 of table 1 completely blocks the basanoid formation with an EC$_{50}$ of less than 200 nM.

Psoriasis Assay

Compounds of the invention are tested form their ability to treat psoriatic skin lesions according to the assay described in Tas & Avci, Pharmacology and Treatment, Dermatology 2004; 209:126-131.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A method of treating a hematological cancer comprising administering to a patient in need thereof a therapeutically effective amount of N-(6-((2R,6S)-2,6-dimethylmorpholino)pyridin-3-yl)-2-methyl-4'-(trifluoromethoxy)biphenyl-3-carboxamide as shown by the below structure

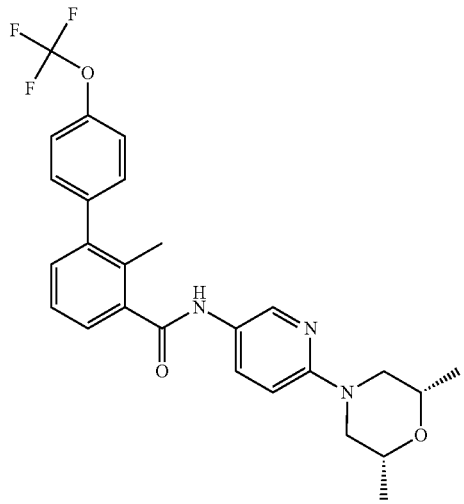 [SMILES: Cc1c(C(=O)Nc2ccc(N3C[C@@H](C)O[C@@H](C)C3)nc2)cccc1-c1ccc(OC(F)(F)F)cc1]

or a pharmaceutically acceptable salt thereof.

2. The method of claim 1, wherein the cancer is plasma cell neoplasm.

3. The method of claim 1, wherein the cancer is leukemia.

4. The method of claim 3, wherein the cancer is childhood leukemia.

5. The method of claim 3, wherein the cancer is chronic lymphocytic leukemia, acute leukemia or chronic leukemia.

6. The method of claim 1, wherein the cancer is lymphoma.

7. The method of claim 6, wherein the cancer is malignant lymphoma.

8. The method of claim 6, wherein the cancer is Hodgkin's lymphoma.

9. The method of claim 6, wherein the cancer is non-Hodgkin's lymphoma, stroma dependent lymphoma, lymphomas of lymphocytic and cutaneous origin, B-cell lymphoma, plasmoblastoma, or plasmacytoma.

10. The method of claim 1, wherein the cancer is multiple myeloma.

* * * * *